(12) United States Patent
Bhattacharya et al.

(10) Patent No.: US 12,383,556 B2
(45) Date of Patent: Aug. 12, 2025

(54) METHODS OF TREATING SJÖGREN'S SYNDROME USING A BRUTON'S TYROSINE KINASE INHIBITOR

(71) Applicant: NOVARTIS AG, Basel (CH)

(72) Inventors: Souvik Bhattacharya, Weymouth, MA (US); Bruno Bieth, Saint-Louis (FR); Maciej Cabanski, Allschwil (CH); Bruno Cenni, Sissach (CH); Stefan De Buck, Buesserach (CH); Martin Kaul, Neustadt (DE); Arvind Kinhikar, Cambridge, MA (US); Andrijana Radivojevic, New York, NY (US); Alessandra Vitaliti Garami, Oberwil (CH)

(73) Assignee: Novartis AG, Basel (CH)

( * ) Notice: Subject to any disclaimer, the term of this patent is extended or adjusted under 35 U.S.C. 154(b) by 874 days.

(21) Appl. No.: 17/612,737

(22) PCT Filed: May 20, 2020

(86) PCT No.: PCT/IB2020/054754
§ 371 (c)(1),
(2) Date: Nov. 19, 2021

(87) PCT Pub. No.: WO2020/234781
PCT Pub. Date: Nov. 26, 2020

(65) Prior Publication Data
US 2022/0175772 A1 Jun. 9, 2022

Related U.S. Application Data

(60) Provisional application No. 62/851,994, filed on May 23, 2019.

(51) Int. Cl.
| A61K 31/505 | (2006.01) |
| A61P 1/02 | (2006.01) |
| A61P 37/06 | (2006.01) |

(52) U.S. Cl.
CPC ............. *A61K 31/505* (2013.01); *A61P 1/02* (2018.01); *A61P 37/06* (2018.01)

(58) Field of Classification Search
CPC ........... A61K 31/505; A61P 1/02; A61P 31/06
See application file for complete search history.

(56) References Cited

U.S. PATENT DOCUMENTS

2017/0174663 A1* 6/2017 Bosanac ................. A61P 19/02
2019/0060462 A1 2/2019 Tengler

FOREIGN PATENT DOCUMENTS

| RU | 2322984 C2 | 4/2008 |
| TW | 201731838 A | 9/2017 |
| WO | 2015/079417 A1 | 6/2015 |
| WO | 2017/106429 A2 | 6/2017 |
| WO | 2017/123695 A1 | 7/2017 |
| WO | 2019/089512 A1 | 5/2019 |
| WO | 2019087094 A1 | 5/2019 |
| WO | 2020234781 A1 | 11/2020 |

OTHER PUBLICATIONS

Seror et al, Ann Rheum Dis 2011; 70: 968-972.*
Mariette et al., N. ENGL J MED 378; 10, pp. 931-939, also including supplemental appendix, Mar. 8, 2018.*
Papas, et al., Novel Anti-CD40 monoclonal antibody CFZ533 in patients with primary Sjogren syndrome: a phase iia double-blind, placebo—controlled randomized trial, Oral surgery, oral medicine, oral pathology and oral radiology, 2018, e203-e204, 126(4).
Pulz, Discovery of LOU064, a covalent BTK inhibitor with best in class selectivity, EFMC-ISMC Symposium Ljubljana, 1-19, Sep. 3, 2018.
Crawford, et al., Discovery of GDC-0853: a potent, selective, and noncovalent Bruton's tyrosine kinase inhibitor in early clinical development, Journal of Medicinal Chemistry, Feb. 19, 2018, 61, 2227-2245.

* cited by examiner

*Primary Examiner* — Rebecca L Anderson
(74) *Attorney, Agent, or Firm* — Francine Li

(57) ABSTRACT

The present disclosure relates to methods for treating Sjögren's Syndrome disease using a compound of Formula (I) or a pharmaceutically acceptable salt thereof. Also disclosed herein a compound of Formula (I) or a pharmaceutically acceptable salt thereof, for treating Sjögren's Syndrome patients, as well as medicaments, dosing regimens, pharmaceutical formulations, dosage forms, and kits for use in the disclosed uses and methods.

21 Claims, 7 Drawing Sheets

Cpd (I) is compound of Formula (I)

Solid line represents Emax model with 95% confidence intervals (shaded area).

METHODS OF TREATING SJÖGREN'S SYNDROME USING A BRUTON'S TYROSINE KINASE INHIBITOR

CROSS-REFERENCE TO RELATED APPLICATIONS

This application is a 371 U.S. National Phase application of International application number PCT/IB2020/054754 filed 20 May 2020, which claims the benefit of U.S. provisional application Ser. No. 62/851,994 filed 23 May 2019.

TECHNICAL FIELD

The present disclosure relates to methods for treating Sjögren's syndrome using a Bruton's tyrosine kinase (BTK) inhibitor.

BACKGROUND OF THE DISCLOSURE

Sjögren's syndrome (SjS) is a systemic autoimmune disease of unknown etiology characterized by lymphoid infiltration and progressive destruction of exocrine glands (Brito-Zerón P., et al, (2016) *Treating the Underlying Pathophysiology of Primary Sjögren Syndrome: Recent Advances and Future Prospects. Drugs* p. 1601-1623).

Although the disease primarily affects the lacrimal and salivary glands, the inflammatory process can target any organ with approximately 15% of patients showing severe extraglandular manifestations (Baldini C., et al (2014) *Primary Sjögren's syndrome as a multi-organ disease: impact of the serological profile on the clinical presentation of the disease in a large cohort of Italian patients. Rheumatology (Oxford)* p. 839-44). The clinical presentation is most often primarily characterized by exocrinopathy of salivary and lacrimal glands presenting with dryness of the mouth and eyes. However, symptoms can be very heterogeneous and range beyond dryness to also include musculoskeletal pain and fatigue affecting nearly all patients, to severe, extraglandular and systemic involvement (characterized by peri-epithelial lymphocytic infiltration and immune complex deposition) in a more limited subset. The mechanism underlying the development of SjS is the destruction of the epithelium of the exocrine glands, as a consequence of autoreactive B cells and T cells (Brito-Zerón P., et al, (2016) *Treating the Underlying Pathophysiology of Primary Sjögren Syndrome: Recent Advances and Future Prospects. Drugs* p. 1601-1623). The high prevalence of autoantibodies, especially against Ro/SSA, even at a very early stage suggests that autoreactive B cells participate in the pathomechanism of SjS (Nocturne G., et al, (2018) *B cells in the pathogenesis of primary Sjögren syndrome. Nat Rev Rheumatol* p. 133-145).

The B-cell pathology also results in an increased risk for malignant transformation, with B-cell lymphomas occurring at a 10-fold elevated lifetime risk in 5% of SjS patients (Baldini C., et al, (2014) *Primary Sjögren's syndrome as a multi-organ disease: impact of the serological profile on the clinical presentation of the disease in a large cohort of Italian patients. Rheumatology (Oxford)* p. 839-44). SjS has an estimated prevalence of 0.3 to 1 per 1,000 persons (Qin B., et al. (2015) *Epidemiology of primary Sjögren's syndrome: a systematic review and meta-analysis. Ann. Rheum. Dis.* p. 1983-9) and is second only to rheumatoid arthritis as a systemic autoimmune disease. The disease affects mainly women with a female/male ratio of 9:1 and can occur at any age. A major effect of the symptoms in SjS is a severe impact on quality of life and productivity, often caused by disabling fatigue associated with the disease (Mariette X., et al.(2018) *Primary Sjögren's Syndrome. N. Engl. J. Med.* p. 931-939). There are also a number of potentially severe systemic complications including arthritis, cutaneous vasculitis, peripheral neuropathy, glomerulonephritis, interstitial nephritis, biliary cholangitis, obstructive bronchiolitis and others, involving multiple organ systems and affecting 20-40% of patients (Seror R., et al (2014) *Outcome measures for primary Sjögren's syndrome: a comprehensive review. J. Autoimmun.* p. 51-6).

Clinical features of Sjögren's syndrome can be divided into medically evaluable and patient-symptomatic manifestations. At the present time, there is no single assessment tool that can capture disease activity of both these clinical manifestations of SjS. Therefore, the "European League Against Rheumatism (EULAR) Sjögren Syndrome (SS) Patient Reported Index" (ESSPRI) and the EULAR SS Disease Activity Index (ESSDAI) are widely accepted as well as validated, to measure symptomatic and systemic manifestations of SjS (Franceschini F., et al, (2017), *BMC Medicine*, 15:69).

In terms of current treatment landscape, there are no internationally approved systemic therapies available for SjS. As far as dryness of mouth and eyes is concerned, treatment for SjS patients is limited to symptomatic care. Steroids and typical DMARDs are mostly ineffective, and no pharmacologic intervention is effective against the severe, disabling fatigue. The lack of effective treatment options underscores the need to evaluate newer therapeutic approaches for this highly debilitating disease. Because the pattern of B cell autoreactivity is to some extent similar to systemic lupus and rheumatoid arthritis, recently, B cell depletion therapy using the anti-CD20 monoclonal antibody (mAb) rituximab has been evaluated for both glandular andextra-glandular manifestations of SjS as well as for lymphoma management with varying degree of success. However, this approach is currently not an approved treatment of SjS. The insufficient efficacy of rituximab could be related to incomplete B cell depletion in the affected tissues (Brito-Zerón P et al (2016) *Treating the Underlying Pathophysiology of Primary Sjögren Syndrome: Recent Advances and Future Prospects. Drugs* p. 1601-1623).

Despite available treatment for SjS, there remains a high medical need for new treatment options for SjS subjects.

SUMMARY OF THE DISCLOSURE

The aim of the invention is to provide a novel method of treating Sjögren's Syndrome disease in a subject in need of such treatment, comprising administering to said subject, a therapeutically effective amount of N-(3-(6-Amino-5-(2-(N-methylacrylamido)ethoxy)pyrimidin-4-yl)-5-fluoro-2-methylphenyl)-4-cyclopropyl-2-fluorobenzamide, or a pharmaceutically acceptable salt thereof.

Therefore, disclosed herein are methods of treating Sjögren's Syndrome (SjS), comprising administering to a subject in need of such treatment, a daily dose of about 0.5 mg to about 600 mg, preferably a daily dose of about 10 mg to about 200 mg, or more preferably a dose of about 10 mg to about 100 mg of N-(3-(6-Amino-5-(2-(N-methylacrylamido)ethoxy)pyrimidin-4-yl)-5-fluoro-2-methylphenyl)-4-cyclopropyl-2-fluorobenzamide, or a pharmaceutically acceptable salt thereof.

Also disclosed is N-(3-(6-Amino-5-(2-(N-methylacrylamido)ethoxy)pyrimidin-4-yl)-5-fluoro-2-methylphenyl)-4-cyclopropyl-2-fluorobenzamide; or a pharmaceutically acceptable salt thereof, for use in treating SjS wherein N-(3-(6-Amino-5-(2-(N-methylacrylamido)ethoxy)pyrimidin-4-yl)-5-fluoro-2-methylphenyl)-4-cyclopropyl-2-fluorobenzamide, or a pharmaceutically acceptable salt thereof is administered in a daily dose of about 0.5 mg to about 600 mg, preferably a daily dose of about 10 mg to about 200 mg, and most preferably in a daily dose of about 10 mg to about 100 mg.

DETAILED DESCRIPTION OF THE DISCLOSURE

Figure 1:
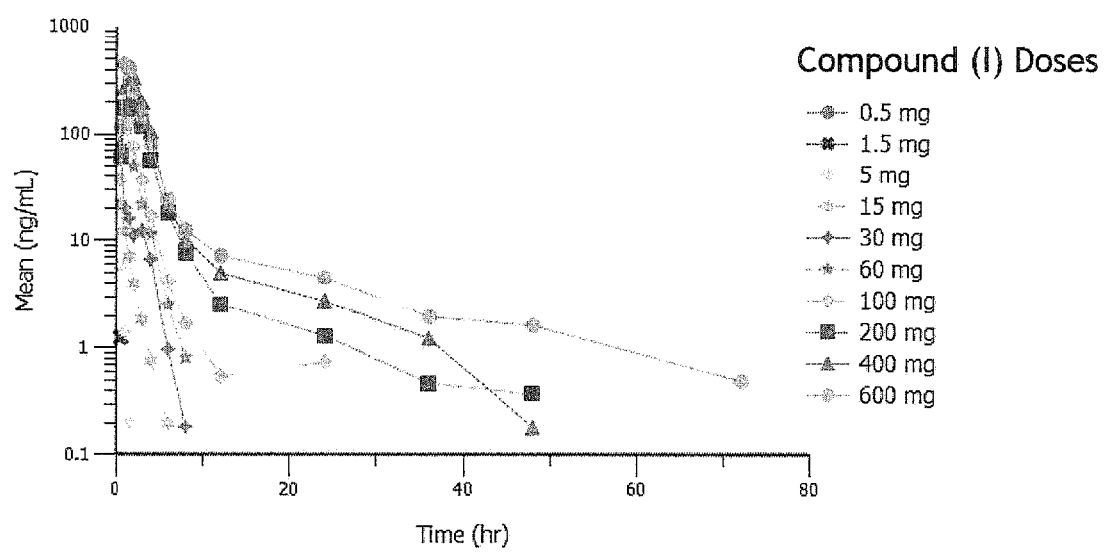
FIG. 1: Blood concentration—time course of compound (I) after single ascending doses 0.5 mg-600 mg

Bruton's tyrosine kinase (BTK) is a cytoplasmic tyrosine kinase and a member of the TEC kinase family. BTK is expressed in cells of both the adaptive and innate immune system including B cells, macrophages, basophils, mast cells and thrombocytes. BTK is indispensable for signaling through the Fc epsilon receptor (FcɛR1 for IgE) and the activating Fc gamma receptors (FcγR for IgG), as well as the B cell antigen receptor (BCR). BTK inhibition has been shown to be an effective concept to treat B cell malignancies. The covalent BTK inhibitors ibrutinib (Imbruvica®), acalabrutinib (Calquence® and zanubrutinib (Brukinsa®) are approved for the treatment of certain B cell malignancies (Thompson P A, et al, (2018) *Bruton's tyrosine kinase inhibitors: first and second generation agents for patients with Chronic Lymphocytic Leukemia (CLL). Expert Opin Investig Drugs* p. 31-42). BTK inhibition has shown promising efficacy on B cell autoimmunity in preclinical and clinical studies (Tan S L., et al, (2013) *Targeting the SYK-BTK axis for the treatment of immunological and hematological disorders: recent progress and therapeutic perspectives. Pharmacol. Ther.* p. 294-309; Whang J. A., et al. (2014) *Bruton's tyrosine kinase inhibitors for the treatment of rheumatoid arthritis. Drug Discov. Today* p. 1200-4; Satterthwaite A. B. (2017) *Bruton's Tyrosine Kinase, a Component of B Cell Signaling Pathways, Has Multiple Roles in the Pathogenesis of Lupus. Front Immunol* p. 1986; Rip J., et al, (2018) The Role of Bruton's Tyrosine Kinase in Immune Cell Signaling and Systemic Autoimmunity. Crit. Rev. Immunol. p. 17-62). Therefore, inhibition of BTK is an attractive therapeutic concept to treat various autoimmune and chronic inflammatory diseases, including rheumatoid arthritis, multiple sclerosis, systemic lupus erythematosus, chronic urticaria, atopic dermatitis, asthma, and primary Sjögren's Syndrome (Tan S L, Liao C, Lucas M C, et al (2013) *Targeting the SYK-BTK axis for the treatment of immunological and hematological disorders: recent progress and therapeutic perspectives. Pharmacol. Ther.* p. 294-309; Whang J A, Chang B Y (2014) *Bruton's tyrosine kinase inhibitors for the treatment of rheumatoid arthritis. Drug Discov. Today* p. 1200-4).

In addition, BTK levels were shown to be increased in circulating B cells of a significant percentage of patients with SjS, in association with high serum rheumatoid factor (RF) levels (Corneth O B J et al. (2017) *Enhanced Bruton's Tyrosine Kinase Activity in Peripheral Blood B Lymphocytes From Patients With Autoimmune Disease.* p. 1313-1324).

N-(3-(6-Amino-5-(2-(N-methylacrylamido)ethoxy)pyrimidin-4-yl)-5-fluoro-2-methylphenyl)-4-cyclopropyl-2-fluorobenzamide, or a pharmaceutically acceptable salt thereof, is a BTK inhibitor referred to herein as Compound of Formula (I):

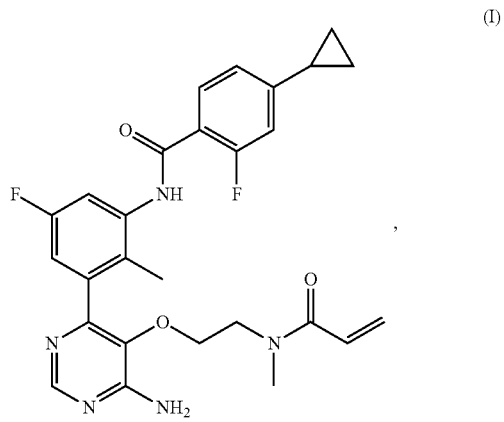 [SMILES: C=CC(=O)N(C)CCOc1c(N)ncnc1-c1cc(F)cc(NC(=O)c2ccc(C3CC3)cc2F)c1C]

or a pharmaceutically acceptable salt thereof.

The compound was described in the WO2015/079417 application filed Jun. 4, 2015. This compound is a selective, potent, irreversible covalent inhibitor of Bruton's tyrosine kinase (BTK), and may be used in a BTK mediated disease or disorder.

Accordingly, we have now devised dosing regimens for treating SjS patients with the compound N-(3-(6-Amino-5-(2-(N-methylacrylamido)ethoxy)pyrimidin-4-yl)-5-fluoro-2-methylphenyl)-4-cyclopropyl-2-fluorobenzamide, or a pharmaceutically acceptable salt thereof.

Definitions

For purposes of interpreting this specification, the following definitions will apply and whenever appropriate, terms used in the singular will also include the plural and vice versa.

The phrase "pharmaceutically acceptable" as employed herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Any formula given herein is also intended to represent unlabeled forms as well as isotopically labeled forms of the compounds. Isotopically labeled compounds have structures depicted by the formulae given herein except that one or more atoms are replaced by an atom having a selected atomic mass or mass number. Isotopes that can be incorporated into compound of the disclosure include, for example, isotopes of hydrogen, carbon, nitrogen, oxygen, fluorine, and chlorine, such as $^3$H, $^{11}$C, $^{13}$C, $^{14}$C, $^{15}$N, $^{18}$F, and $^{36}$Cl. Accordingly, it should be understood that the present disclosure includes compound that incorporates one or more of any of the aforementioned isotopes, including for example, radioactive isotopes, such as $^3$H and $^{14}$C, or those into which non-radioactive isotopes, such as $^2$H and $^{13}$C are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically-labeled compounds can generally be prepared by conventional techniques known to those skilled in the art, e.g., using an appropriate isotopically-labeled reagents in place of the non-labeled reagent previously employed.

The term "pharmaceutical combination" as used herein means a product that results from the use or mixing or combining of more than one active ingredient. It should be understood that pharmaceutical combination as used herein includes both fixed and non-fixed combinations of the active ingredients. The term "fixed combination" means that the active ingredients, e.g., a compound of formula (I) or a pharmaceutically acceptable salt thereof, and one or more combination partners, are administered to a patient simultaneously as a single entity or dosage form. The term in such case refers to a fixed dose combination in one unit dosage form (e.g., capsule, tablet, or sachet). The terms "non-fixed combination" or a "kit of parts" both mean that the active ingredients, e.g., a compound of the present disclosure and one or more combination partners and/or one or more co-agents, are administered or co-administered to a patient independently as separate entities either simultaneously, concurrently or sequentially with no specific time limits wherein such administration provides therapeutically effective levels of the two compounds in the body of the patient, especially where these time intervals allow that the combination partners show a cooperative, e.g., an additive or synergistic effect. The term "non-fixed combination" also applies to cocktail therapy, e.g., the administration of three or more active ingredients. The term "non-fixed combination" thus defines especially administration, use, composition or formulation in the sense that the compound described herein can be dosed independently of each other, i.e., simultaneously or at different time points. It should be understood that the term "non-fixed combination" also encompasses the use of a single agent together with one or more fixed combination products with each independent formulation having distinct amounts of the active ingredients contained therein. It should be further understood that the combination products described herein as well as the term "non-fixed combinations" encompasses active ingredients (including the compounds described herein) where the combination partners are administered as entirely separate pharmaceutical dosage forms or as pharmaceutical formulations that are also sold independently of each other. Instructions for the use of the non-fixed combination are or may be provided in the packaging, e.g., leaflet or the like, or in other information that is provided to physicians and/or medical staff. The independent formulations or the parts of the formulation, products, or compositions, can then be administered simultaneously or chronologically staggered, that is the individual parts of the kit of parts can each be administered at different time points and/or with equal or different time intervals for any part of the kit of parts. Particularly, the time intervals for the dosing are chosen such that the effect on the treated disease with the combined use of the parts is larger/greater than the effect obtained by use of only compound of Formula (I); thus the compounds used in pharmaceutical combination described herein are jointly active. The ratio of the total amounts of a compound of formula I to a second agent to be administered as a pharmaceutical combination can be varied or adjusted in order to better accommodate the needs of a particular patient subpopulation to be treated or the needs of the single patient, which can be due, for example, to age, sex, body weight, etc. of the patients.

The terms "co-administration" or "combined administration" or the like as utilized herein are meant to encompass the administration of one or more compounds described herein together with a selected combination partner to a single subject in need thereof (e.g., a patient or subject), and are intended to include treatment regimens in which the compounds are not necessarily administered by the same route of administration and/or at the same time.

The term "pharmaceutical composition" is defined herein to refer to a mixture (e.g., a solution or an emulsion) containing at least one active ingredient or therapeutic agent to be administered to a warm-blooded animal, e.g., a mammal or human, in order to prevent or treat a particular disease or condition affecting the warm-blooded animal.

The term "a therapeutically effective amount" of a compound (i.e. compound of Formula (I) or a pharmaceutically acceptable salt thereof) of the present disclosure refers to an amount of the compound of the present disclosure that will elicit the biological or medical response of a subject (patient of subject), for example, reduction or inhibition of an enzyme or a protein activity, or ameliorate symptoms, alleviate conditions, slow or delay disease progression, or prevent a disease, etc. The therapeutically effective dosage of a compound, the pharmaceutical composition, or the combinations thereof, is dependent on the species of the patient, the body weight, age, sex, and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

Frequency of dosage may vary depending on the compound used and the particular condition to be treated or prevented. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

As used herein, the term "carrier" or "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

As used herein, the term "subject" refers to an animal. Typically, the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In a preferred embodiment, the subject is a human. The term "subject" is used interchangeably with "patient" when it refers to human.

As used herein, a subject is "in need of" a treatment if such subject would benefit biologically, medically or in quality of life from such treatment.

As used herein, the phrase "population of patients" is used to mean a group of patients.

The term "comprising" encompasses "including" as well as "consisting," e.g., a composition "comprising" X may consist exclusively of X or may include something additional, e.g., X+Y.

The term "about" in relation to a numerical value x means, for example, +/−10%. When used in front of a numerical range or list of numbers, the term "about" applies to each number in the series, e.g., the phrase "about 1-5" should be interpreted as "about 1-about 5", or, e.g., the phrase "about 1, 2, 3, 4" should be interpreted as "about 1, about 2, about 3, about 4, etc."

The term "treatment" or "treat" is herein defined as the application or administration of a compound according to the disclosure, (compound of Formula (I), or a pharmaceutically acceptable salt thereof, or a pharmaceutical composition comprising said compound, to a subject or to an isolated tissue or cell line from a subject, where the subject has a particular disease (e.g., SjS), a symptom associated with the disease (e.g., SjS), or a predisposition towards development of the disease (e.g., SjS) (if applicable), where the purpose is to cure (if applicable), delay the onset of, reduce the severity of, alleviate, ameliorate one or more symptoms of the disease, improve the disease, reduce or improve any associated symptoms of the disease or the predisposition toward the development of the disease. The term "treatment" or "treat" includes treating a patient suspected to have the disease as well as patients who are ill or who have been diagnosed as suffering from the disease or medical condition, and includes suppression of clinical relapse.

As used herein, "selecting" and "selected" in reference to a patient is used to mean that a particular patient is specifically chosen from a larger group of patients on the basis of (due to) the particular patient having a predetermined criteria. Similarly, "selectively treating" refers to providing treatment to a patient having a particular disease, where that patient is specifically chosen from a larger group of patients on the basis of the particular patient having a predetermined criterion. Similarly, "selectively administering" refers to administering a drug to a patient that is specifically chosen from a larger group of patients on the basis of (due to) the particular patient having a predetermined criterion. By "selecting", "selectively treating" and "selectively administering", it is meant that a patient is delivered a personalized therapy based on the patient's personal history (e.g., prior therapeutic interventions, e.g., prior treatment with biologics), biology (e.g., particular genetic markers), and/or manifestation (e.g., not fulfilling particular diagnostic criteria), rather than being delivered a standard treatment regimen based solely on the patient's membership in a larger group. Selecting, in reference to a method of treatment as used herein, does not refer to fortuitous treatment of a patient having a particular criterion, but rather refers to the deliberate choice to administer treatment to a patient based on the patient having a particular criterion. Thus, selective treatment/administration differs from standard treatment/administration, which delivers a particular drug to all patients having a particular disease, regardless of their personal history, manifestations of disease, and/or biology. In some embodiments, the patient was selected for treatment based on having SjS.

Embodiments of the Invention

Sjorgren Syndrome and Effectiveness of Treatment According to the Invention

The disclosed BTK inhibitor, i.e., compound of Formula (I), or a pharmaceutically acceptable salt thereof, may be used in vitro, ex vivo, or incorporated into pharmaceutical compositions and administered in vivo to treat SjS patients (e.g., human patients).

The effectiveness of a Sjögren's treatment may be assessed using various known methods and tools that measure Sjögren's Syndrome state and/or Sjögren's clinical response. Some examples include, e.g., EULAR Sjögren's Syndrome Disease Activity Index (ESSDAI), Physician Global Assessment Scale (PhGA), EULAR Sjögren's Syndrome Patient Reported Index (ESSPRI), The Functional Assessment of Chronic Illness Therapy-Fatigue Scale (FACIT-Fatigue) and EQ5D.

Efficacy

Clinical efficacy measurements related to primary and secondary objectives are outlined below.

EULAR Sjögren's Syndrome Disease Activity Index (ESSDAI)

ESSDAI is a validated disease outcome measure for Sjögren's Syndrome and is applied to the study subjects (Seror R, et al (2015) *Validation of EULAR primary Sjögren's syndrome disease activity (ESSDAI) and patient indexes (ESSPRI)*. *Ann. Rheum. Dis.* p. 859-66). The instrument contains 12 organ-specific domains contributing to disease activity. For each domain, features of disease activity are scored in 3 or 4 levels according to their severity. These scores are then summed across the 12 domains in a weighted manner to provide the total score. The domains (weights) are as follows: constitutional (3), lymphadenopathy (4), glandular (2), articular (2), cutaneous (3), pulmonary (5), renal (5), muscular (6), PNS (5), CNS (5), hematological (2), and biological (1). The maximum possible score is 123.

In our study, to calculate ESSDAI, all 12 organ domains must be individually assessed at every scheduled timepoint (from screening visit till end of study). Domain assessments are entered into a table (provided by a central vendor) and ESSDAI score is calculated by the software.

For assessments not listed in the protocol as mandatory tests but which may be needed to estimate ESSDAI, including radiography, high resolution computer tomography (HRCT), lung function test (DLCO, FVC), estimated glomerular filtration rate (eGFR), electromyography (EMG), muscle (or any other) biopsy, it is at the investigator's discretion to have these assessed based on the signs and symptoms of the patient so to provide correct ESSDAI readout. The EULAR Sjorgen syndrome disease index (ES-SDAI), domain and item definitions and weights are summarized in table 1:

| Domain [weight] | Activity level | Description |
|---|---|---|
| Constitutional [3] Exclusion of fever of infectious origin and voluntary weight loss | No = 0 Low = 1 Moderate = 2 | Absence of the following symptoms Mild or intermittent fever (37.5-38.5° C.)/night sweats and/or involuntary weight loss of 5-10% of body weight Severe fever (>38.5° C.)/night sweats and/or involuntary weight loss of >10% of body weight |
| Lymphadenopathy [4] Exclusion of infection | No = 0 Low = 1 Moderate = 2 High = 3 | Absence of the following features Lymphadenopathy ≥1 cm in any nodal region or ≥2 cm in inguinal region Lymphadenopathy ≥2 cm in any nodal region or ≥3 cm in inguinal region, and/or splenomegaly (clinically palpable or assessed by imaging) Current malignant B-cell proliferative disorder |
| Glandular [2] Exclusion of stone or infection | No = 0 Low = 1 Moderate = 2 | Absence of glandular swelling Small glandular swelling with enlarged parotid (≤3 cm), or limited submandibular or lachrymal swelling Major glandular swelling with enlarged parotid (>3 cm), or important submandibular or lachrymal swelling |
| Articular [2] Exclusion of osteoarthritis | No = 0 Low = 1 Moderate = 2 High = 3 | Absence of currently active articular involvement Arthralgias in hands, wrists, ankles and feet accompanied by morning stiffness (>30 min) 1-5 (of 28 total count) synovitis ≥6 (of 28 total count) synovitis |
| Cutaneous [3] Rate as 'no activity' stable long-lasting features related to damage | No = 0 Low = 1 Moderate = 2 High = 3 | Absence of currently active cutaneous involvement Erythema multiforma Limited cutaneous vasculitis, including urticarial vasculitis, or purpura limited to feet and ankle, or subacute lutaneous lupus Diffuse cutaneous vasculitis, including urticarial vasculitis, or diffuse purpura, or ulcers related to vasculitis |
| Pulmonary* [5] Rate as 'no activity' stable long-lasting features related to damage, or respiratory involvement not related to the disease (tobacco use, etc) | No = 0 Low = 1 Moderate = 2 High = 3 | Absence of currently active pulmonary involvement Persistent cough or bronchial involvement with no radiographic abnormalities on radiography or radiological or HRCT evidence of interstitial lung disease with no breathlessness and normal lung function test Moderately active pulmonary involvement, such as interstitial lung disease shown by HRCT with shortness of breath on exercise (NYHA II) or abnormal lung function tests restricted to 70% > $DL_{CO}$ ≥ 40% or 80% > FVC ≥ 60% Highly active pulmonary involvement, such as interstitial lung disease shown by HRCT with shortness of breath at rest (NHYA III, IV) or with abnormal lung function tests $DL_{CO}$ < 40% or FVC < 60% |
| Renal [5] Rate as 'no activity' stable long-lasting features related to damage and renal involvement not related to the disease. If biopsy has been performed, please rate activity based on histological features first | No = 0 Low = 1 Moderate = 2 High = 3 | Absence of currently active renal involvement with proteinuria <0.5 g/day, no haematuria, no leucocyturia, no acidosis, or long-lasting stable proteinuria due to damage Evidence of mild active renal involvement, limited to tubular acidosis without renal failure or glomerular involvement with proteinuria (between 0.5 and 1 g/day) and without haematuria or renal failure (GFR ≥60 ml/min) Moderately active renal involvement, such as tubular acidosis with renal failure (GFR <60 ml/min) or glomerular involvement with proteinuria between 1 and 1.5 g/day and without haematuria or renal failure (GFR ≥60 ml/min) or histological evidence of extra-membranous glomerulonephritis or important interstitial lymphoid infiltrate Highly active renal involvement, such as glomerular involvement with proteinuria >1.5 g/day or haematuria or renal failure (GFR <60 ml/min), or histological evidence of proliferative glomerulonephritis or cryoglobulinaemia-related renal involvement |
| Muscular* [6] Exclusion of weakness due to corticosteroids | No = 0 Low = 1 Moderate = 2 High = 3 | Absence of currently active muscular involvement Mild active myositis shown by abnormal EMG or biopsy with no weakness and creatine kinase (N < CK ≤ 2N) Moderately active myositis confirmed by abnormal EMG or biopsy with weakness (maximal deficit of 4/5), or elevated creatine kinase (2N <CK <4N) Highly active myositis shown by abnormal EMG or biopsy with weakness (deficit ≤3/5) or elevated creatine kinase (>4N) |
| PNS* [5] Rate as 'no activity' stable long-lasting features related to damage or PNS involvement not related to the disease | No = 0 Low = 1 Moderate = 2 High = 3 | Absence of currently active PNS involvement Mild active peripheral nervous system involvement, such as pure sensory axonal polyneuropathy shown by NCS or trigeminal (V) neuralgia Moderately active peripheral nervous system involvement shown by NCS, such as axonal sensorimotor neuropathy with maximal |

| Domain [weight] | Activity level | Description |
|---|---|---|
| | | motor deficit of 4/5, pure sensory neuropathy with presence of cryoglobulinamic vasculitis, ganglionopathy with symptoms restricted to mild/moderate ataxia, inflammatory demyelinating polyneuropathy (CIDP) with mild functional impairment (maximal motor deficit of 4/5 or mild ataxia) Or cranial nerve involvement of peripheral origin (except trigeminal (V) neuralgia) Highly active PNS involvement shown by NCS, such as axonal sensorimotor neuropathy with motor deficit ≤3/5, peripheral nerve involvement due to vasculitis (mononeuritis multiplex, etc), severe ataxia due to ganglionopathy, inflammatory demyelinating polyneuropathy (CIDP) with severe functional impairment: motor deficit ≤3/5 or severe ataxia |
| CNS* [5] Rate as 'no activity' stable long-lasting features related to damage or CNS involvement not related to the disease | No = 0 High = 3 | Absence of currently active CNS involvement Highly active CNS features, such as cerebral vasculitis with cerebrovascular accident or transient ischaemic attack, seizures, transverse myelitis, lymphocytic meningitis, multiple sclerosis-like syndrome with motor deficit |
| Haematological [2] For anaemia, neutropenia, and thrombopenia, only autoimmune cytopenia must be considered Exclusion of vitamin or iron deficiency, drug-induced cytopenia | No = 0 Low = 1 Moderate = 2 High = 3 | Absence of auto-immune cytopenia Cytopenia of auto-immune origin with neutropenia (1000 < neutrophils < 1500/mm3), and/or anaemia (10 < haemoglobin < 12 g/dl), and/or thrombocytopenia (100000 < platelets < 150000/mm3) Or lymphopenia (500 < lymphocytes < 1000/mm3) Cytopenia of auto-immune origin with neutropenia (500 ≤ neutrophils ≤ 1000/mm3), and/or anaemia (8 ≤ haemoglobin ≤ 10 g/dl), and/or thrombocytopenia (50000 ≤ platelets ≤ 100000/mm3) Or lymphopenia (≤500/mm3) Cytopenia of auto-immune origin with neutropenia (neutrophils < 500/mm3), and/or or anaemia (haemoglobin < 8 g/dl) and/or thrombocytopenia (platelets < 50000/mm3) |
| Biological [1] | No = 0 Low = 1 Moderate = 2 | Absence of any of the following biological features Clonal component and/or hypocomplementaemia (low C4 or C3 or CH50) and/or hypergammaglobulinaemia or high IgG level between 16 and 20 g/l Presence of cryoglobulinaemia and/or hypergammaglobulinaemia or high IgG level >20 g/l, and/or recent onset hypogammaglobulinaemia or recent decrease of IgG level (<5 g/l) |

Physician Global Assessment Scale (PhGA)

The physician's global assessment scale is used by the Investigator to rate the disease activity of their patient using 100 mm VAS ranging from "no disease activity" (0) to "maximal disease activity" (100).

To enhance objectivity, the physician must not be aware of the specific patient's reported outcome assessments, when performing his own assessment on that patient. Therefore this assessment must be done prior to viewing the patient's global assessment of overall disease activity score.

EULAR Sjögren's Syndrome Patient Reported Index (ESSPRI)

ESSPRI is an established disease outcome measure for Sjögren's Syndrome (Seror R, et al (2011) *EULAR Sjögren's Syndrome Patient Reported Index (ESSPRI): development of a consensus patient index for primary Sjögren's syndrome. Ann. Rheum. Dis.* p. 968-72). It consists of three of domains of dryness, pain and fatigue. The subject can assess severity of symptoms they experience on a single 0-10 numerical scale for each of the three domains. The ESSPRI score is defined as mean of scores from the three scales: (dryness+pain+fatigue)/3.

FACIT-Fatigue

The Functional Assessment of Chronic Illness Therapy-Fatigue Scale (FACIT-F v4) is a short, 13-item, easy-to-administer tool that measures an individual's level of fatigue during their usual daily activities over the past week. The level of fatigue is measured on a 5-point Likert scale (0=not at all, 1=a little bit, 2=somewhat, 3=quite a bit, 4=very much) (Webster K, et al. (2003) *The Functional Assessment of Chronic Illness Therapy (FACIT) Measurement System: properties, applications, and interpretation. Health Qual Life Outcomes* p. 79).

EQ5D

EQ-5D is a standardized instrument which measures the health-related quality of life.

The EQ-5D consists of a descriptive system and the EQ VAS scale.

The descriptive system comprises five dimensions: mobility, self-care, usual activities, pain/discomfort and anxiety/depression. This can be used as a quantitative measure of health outcome that reflects the patient's own judgement. The scores on these five dimensions can be presented as a health profile or can be converted to a single summary index number (utility) reflecting preferability compared to other health profiles.

The EQ VAS records the patient's self-rated health on a vertical visual analogue scale with 0 representing 'Worst imaginable Health State' and 100 'Best imaginable Health State'.

Appropriateness of Efficacy Assessments

Efficacy measures in this study are primarily based on ESSDAI (EULAR SS Disease Activity Index) measuring organ-specific disease criteria, and on ESSPRI (European League Against Rheumatism [EULAR] Sjögren Syndrome [SS] Patient Reported Index) measuring the patient's subjective disease impact. Both instruments are widely accepted and validated, gold-standard measures of systemic and symptomatic manifestations of SjS, respectively. ESSDAI is a systemic disease activity index that classifies disease activity in 3-4 levels, over each of 12 differentially weighted domains (biologic, hematologic, articular, glandular, cutaneous, constitutional, lymphadenopathy, renal, pulmonary, PNS, CNS and muscular). A composite weighted score provides an accurate assessment of disease activity, with a good sensitivity to change, as validated in multiple cohort studies (Seror R et al (2015) *Validation of EULAR primary Sjögren's syndrome disease activity (ESSDAI) and patient indexes (ESSPRI). Ann. Rheum. Dis.* p. 859-66). The ESSPRI tool, on the other hand, is a patient reported composite score of symptoms of dryness, limb pain and fatigue evaluated on 0-10 visual analog scale, during the preceeding 2 weeks (Seror R et al (2011) *EULAR Sjögren's Syndrome Patient Reported Index (ESSPRI): development of a consensus patient index for primary Sjögren's syndrome. Ann. Rheum. Dis.* p. 968-72). Patient reported scores have poor sensitivity to change in disease activity, but among available tools, ESSPRI has been reported to have significantly better sensitivity. A recent prospective study reported poor correlation between systemic and patient scores, suggesting that the two indices evaluate complementary components of disease activity, therefore underscoring the importance of evaluation of both parameters to arrive at an accurate assessment of disease activity and change thereof (Seror R et al (2015) *Validation of EULAR primary Sjögren's syndrome disease activity (ESSDAI) and patient indexes (ESSPRI). Ann. Rheum. Dis.* p. 859-66).

Pharmaceutical Composition

The BTK inhibitor, i.e., compound of Formula (I), or a pharmaceutically acceptable salt thereof, may be used as a pharmaceutical composition when combined with a pharmaceutically acceptable carrier. Such a composition may contain, in addition to the compound of Formula (I), carriers, various diluents, fillers, salts, buffers, stabilizers, solubilizers, and other materials known in the art. The characteristics of the carrier depends on the route of administration. The pharmaceutical compositions for use in the disclosed methods may also contain additional therapeutic agents for treatment of the particular targeted disorder. For example, a pharmaceutical composition may also include anti-inflammatory or anti-itch agents. Such additional factors and/or agents may be included in the pharmaceutical composition to produce a synergistic effect with the compound of Formula (I), or to minimize side effects caused by the compound of Formula (I). In preferred embodiments, the pharmaceutical composition for use in the disclosed methods comprise compound of Formula (I) in a dose of 10 mg, 20 mg, 25 mg, 50 mg or about 100 mg.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients, which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Pharmaceutical compositions for use in the disclosed methods may be manufactured in conventional manner. In one embodiment, the pharmaceutical composition is provided for oral administration. For example the pharmaceutical compositions are tablets or gelatin capsules comprising the active ingredient together with
   a) diluents, e.g., lactose, dextrose, sucrose, mannitol, sorbitol, cellulose and/or glycine;
   b) lubricants, e.g., silica, talcum, stearic acid, its magnesium or calcium salt and/or polyethyleneglycol; for tablets also
   c) binders, e.g., magnesium aluminum silicate, starch paste, gelatin, tragacanth, methylcellulose, sodium carboxymethylcellulose and/or polyvinylpyrrolidone; if desired
   d) disintegrants, e.g., starches, agar, alginic acid or its sodium salt, or effervescent mixtures; and/or
   e) absorbents, colorants, flavors and sweeteners.
Tablets may be either film coated or enteric coated according to methods known in the art.

Combinations

In practicing some of the methods of treatment or uses of the present disclosure, a therapeutically effective amount of a compound of Formula (I) or a pharmaceutically acceptable salt thereof, is administered to a patient, e.g., a mammal (e.g., a human). While it is understood that the disclosed methods provide for the treatment of Sjögren's patients using compound of Formula (I) or a pharmaceutically acceptable salt thereof, the therapy is not necessarily a monotherapy. Indeed, if a patient is selected for the treatment with a compound of Formula (I), then the compound of Formula (I) or a pharmaceutically acceptable salt thereof, may be administered in accordance with the methods of the disclosure either alone or in combination with other agents and therapies for treating Sjögren's patients, e.g., in combination with at least one additional Sjögren's agent. When co-administered with one or more additional SjS agent(s), a compound of Formula (I) or a pharmaceutically acceptable salt thereof, may be administered either simultaneously with the other agent, or sequentially. If administered sequentially, the attending physician will decide on the appropriate sequence of administering the compound of Formula (I) or a pharmaceutically acceptable salt thereof, in combination with other agents and the appropriate dosages for co-delivery.

Various therapies may be beneficially combined with the disclosed compound of Formula (I) or a pharmaceutically acceptable salt thereof, during treatment of SjS. Such therapies include steroids (corticosteroid such as prednisone or equivalent); DMARDSs such as for example hydroxychloroquine (Plaquenil), methotrexate (Trexall), sulfasalazine (Azulfidine), minocycline (Minocin) or leflunomide (Arava)); or B-cell depleting drug such as Rituximab.

A skilled artisan will be able to discern the appropriate dosages of the above SjS agents for co-delivery with the disclosed compound of Formula (I) or a pharmaceutically acceptable salt thereof.

Kits of the Invention

The disclosure also encompasses kits for treating SjS. Such kits comprise a BTK inhibitor, e.g., N-(3-(6-Amino-5-(2-(N-methylacrylamido)ethoxy)pyrimidin-4-yl)-5-fluoro-2-methylphenyl)-4-cyclopropyl-2-fluorobenzamide or a pharmaceutical composition thereof. Additionally, such kits may comprise instructions for use.

In one embodiment, the kit comprises two or more two or more separate pharmaceutical compositions, at least one of which contains a compound of Formula (I) or a pharmaceutically acceptable salt thereof. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of Formula (I) or a pharmaceutically acceptable salt thereof, and the other SjS agent (as defined herein) may be manufactured and/or formulated by the same or different manufacturers. Moreover, the compound of Formula (I) or a pharmaceutically acceptable salt thereof, and the other SjS agent may be brought together into a combination therapy: (i) prior to release of the combination product to physicians (e.g. in the case of a kit comprising a compound of Formula (I) or a pharmaceutically acceptable salt thereof, and the other SjS agent); (ii) by the physician themselves (or under the guidance of the physician) shortly before administration; (iii) in the patient themselves, e.g. during sequential administration of the compound of Formula (I) or a pharmaceutically acceptable salt thereof, and the other SjS agent.

Additional Embodiments

A compound of Formula (I) or a pharmaceutically acceptable salt thereof, is conveniently administered to a patient (preferably orally) in a dose of about 10 mg to about 200 mg daily.

A compound of Formula (I) or a pharmaceutically acceptable salt thereof, is conveniently administered to a patient (preferably orally) in a daily dose of about 10 mg to about 200 mg daily.

In some embodiments, the compound of Formula (I) or a pharmaceutically acceptable salt thereof, is administered in a daily dose of about 10 mg to about 100 mg.

In other embodiments, the compound of Formula (I) or a pharmaceutically acceptable salt thereof, is administered in a daily dose of about 100 mg.

In other embodiments, the compound of Formula (I) or a pharmaceutically acceptable salt thereof, is administered in a daily dose of about 50 mg.

In other embodiments, the compound of Formula (I) or a pharmaceutically acceptable salt thereof, is administered in a daily dose of about 35 mg.

In other embodiments, the compound of Formula (I) or a pharmaceutically acceptable salt thereof, is administered in a daily dose of about 25 mg.

In other embodiments, the compound of Formula (I) or a pharmaceutically acceptable salt thereof, is administered in a daily dose of about 20 mg.

In one embodiment, compound of Formula (I) or a pharmaceutically acceptable salt thereof, is administered once daily in a dose of about 10 mg, about 35 mg, about 50 mg or about 100 mg.

In another embodiment, compound of Formula (I) or a pharmaceutically acceptable salt thereof, is administered twice daily in a dose of about 10 mg, about 25 mg, about 50 mg or about 100 mg.

It will be understood that dose escalation may be required for certain patients, e.g., Sjögren's patients that display inadequate response (e.g., as measured by any of the Sjögren's scoring systems disclosed herein. It will also be understood that dose reduction may also be required for certain patients, e.g., Sjögren's patients that display adverse events or an adverse response to treatment with compound of Formula (I) or a pharmaceutically acceptable salt thereof. Thus, dosages of the compound of Formula (I) or a pharmaceutically acceptable salt thereof, may be less than about 10 mg, about 20 mg, about 25 mg, about 50 mg, or about 100 mg.

The timing of dosing is generally measured from the day of the first dose of compound of Formula (I), or a pharmaceutically acceptable salt thereof (which is also known as "baseline"). The timing of dosing is generally measured from the day of the first dose of Compound of Formula (I), or a pharmaceutically acceptable salt thereof (which is also known as "baseline").

However, health care providers often use different naming conventions to identify dosing schedules. For clarification, as disclosed herein, the first day of dosing is referred to as day 1. However, it will be understood by a skilled artisan that this naming convention is simply used for consistency and should not be construed as limiting, i.e., daily dosing is the provision of a daily dose of the compound of Formula (I) or a pharmaceutically acceptable salt thereof and the physician may refer to a particular day as "day 0" or "day 1".

Disclosed herein are methods of treating Sjögren's Syndrome disease (SjS), comprising administering to a patient in need thereof, a compound of Formula (I), or a pharmaceutically acceptable salt thereof, wherein the dose is about 10 mg-about 200 mg.

Also disclosed herein are methods of treating Sjögren's Syndrome disease (SjS), comprising administering to a patient in need thereof, a compound of Formula (I), or a pharmaceutically acceptable salt thereof, wherein the daily dose is about 10 mg-about 200 mg.

Also disclosed herein is a compound of Formula (I), or a pharmaceutically acceptable salt thereof, for use in treating SjS, wherein the daily dose of the compound is about 10 mg-about 200 mg.

In one embodiment of the disclosed methods, uses and kits, the compound of Formula (I), or a pharmaceutically acceptable salt thereof, is administered in a daily dose of about 10 mg to about 100 mg.

In another embodiment of the disclosed methods, uses and kits, the compound of Formula (I), or a pharmaceutically acceptable salt thereof, is administered in a daily dose of about 10 mg, about 20 mg, about 25 mg, about 35 mg, about 50 mg, about 100 mg or about 200 mg.

In another embodiment of the disclosed methods, uses and kits, the compound of Formula (I), or a pharmaceutically acceptable salt thereof, is administered in a daily dose of about 100 mg.

In another embodiment of the disclosed methods, uses and kits, the compound of Formula (I), or a pharmaceutically acceptable salt thereof, is administered in a daily dose of about 50 mg.

In another embodiment of the disclosed methods, uses and kits, the compound of Formula (I), or a pharmaceutically acceptable salt thereof, is administered in a daily dose of about 35 mg.

In another embodiment of the disclosed methods, uses and kits, the compound of Formula (I), or a pharmaceutically acceptable salt thereof, is administered in a daily dose of about 25 mg.

In another embodiment of the disclosed methods, uses and kits, the compound of Formula (I), or a pharmaceutically acceptable salt thereof, is administered in a daily dose of about 20 mg.

In another embodiment of the disclosed methods, uses and kits, the compound of Formula (I), or a pharmaceutically acceptable salt thereof, is administered once daily in a dose of about 10 mg, about 35 mg, about 50 mg, or about 100 mg.

In another embodiment of the disclosed methods, uses and kits, the compound of Formula (I), or a pharmaceutically acceptable salt thereof, is administered in a dose of about 10 mg, about 25 mg, about 50 mg, or about 100 mg twice a day.

In another embodiment of the disclosed methods, uses and kits, the patient has moderate to severe SjS. A patient with moderate to severe SjS is defined as a patient having prior to treatment with the compound of Formula (I) or a pharmaceutically acceptable salt thereof, an ESSDAI score (based on weighted score as shown in table 1)≥5 (i.e. at least 5) from 8 defined domains (biologic, hematologic, articular, cutaneous, glandular, lymphadenopathy, renal, constitutional) and an ESSPRI score of at least 5.

In another embodiment of the disclosed methods, uses and kits, the patient is an adult.

In another embodiment of the disclosed methods, uses and kits, the patient achieves by week 12 or by week 24 of treatment a change from baseline on at least one of the patient and/or physician-reported outcomes (i.e. ESSPRI, FACIT-F, EQ-5D, PhGA).

In another embodiment of the disclosed methods, uses and kits, the patient achieves by week 12 or by week 24 of treatment a change from baseline of the ESSPRI score.

In another embodiment of the disclosed methods, uses and kits, the patient achieves by week 12 or by week 24 of treatment a reduction of the ESSPRI score.

In another embodiment of the disclosed methods, uses and kits, the patient achieves by week 12 or by week 24 of treatment a reduction of the ESSPRI score by at least one point, preferably at least 2 points.

In another embodiment of the disclosed methods, uses and kits, the patient achieves by week 12 or by week 24 of treatment a reduction of the the ESSPRI score. In another embodiment of the disclosed methods, uses and kits, the patient achieves by week 12 or by week 24 of treatment a reduction of at least 15%, at least 25%, at least 35%, at least 50% or at least 60% in the ESSPRI score. A reduction of the ESSPRI score is calculated as:

$$\left(1 - \frac{ESSPRI \text{ after treatment}}{ESSPRI \text{ prior to treatment}}\right) \times 100$$

In another embodiment of the disclosed methods, uses and kits, the patient achieves by week 12 or by week 24 of treatment a reduction of the ESSDAI score.

In yet another embodiment of the disclosed methods, uses and kits, the patient achieves by week 12 or by week 24 of treatment a reduction of the ESSDAI score by at least 3 points.

In another embodiment of the disclosed methods, uses and kits, the patient achieves by week 12 or by week 24 of treatment a change from baseline of the ESSDAI score.

In preferred embodiments of the disclosed methods, uses and kits, the patient is an adult. In some embodiments of the disclosed methods, uses and kits, the patient is an adolescent.

Further Enumerated Embodiments

1. A method of treating Sjögren's syndrome (SjS), comprising administering to a subject in need thereof a daily dose of about 10 mg-about 200 mg of N-(3-(6-Amino-5-(2-(N-methylacrylamido)ethoxy)pyrimidin-4-yl)-5-fluoro-2-methylphenyl)-4-cyclopropyl-2-fluorobenzamide, or a pharmaceutically acceptable salt thereof.
2. The method according to embodiment 1, wherein the daily dose of N-(3-(6-Amino-5-(2-(N-methylacrylamido)ethoxy)pyrimidin-4-yl)-5-fluoro-2-methylphenyl)-4-cyclopropyl-2-fluorobenzamide, or a pharmaceutically acceptable salt thereof is about 10 mg to about 100 mg.
3. The method according to embodiment 1, wherein the daily dose of N-(3-(6-Amino-5-(2-(N-methylacrylamido)ethoxy)pyrimidin-4-yl)-5-fluoro-2-methylphenyl)-4-cyclopropyl-2-fluorobenzamide, or a pharmaceutically acceptable salt thereof is about 100 mg.
4. The method according to embodiment 1, wherein the daily dose of N-(3-(6-Amino-5-(2-(N-methylacrylamido)ethoxy)pyrimidin-4-yl)-5-fluoro-2-methylphenyl)-4-cyclopropyl-2-fluorobenzamide, or a pharmaceutically acceptable salt thereof is about 50 mg.
5. The method according to embodiment 1, wherein the daily dose of N-(3-(6-Amino-5-(2-(N-methylacrylamido)ethoxy)pyrimidin-4-yl)-5-fluoro-2-methylphenyl)-4-cyclopropyl-2-fluorobenzamide, or a pharmaceutically acceptable salt thereof is about 35 mg.
5. The method according to embodiment 1, wherein the daily dose of N-(3-(6-Amino-5-(2-(N-methylacrylamido)ethoxy)pyrimidin-4-yl)-5-fluoro-2-methylphenyl)-4-cyclopropyl-2-fluorobenzamide, or a pharmaceutically acceptable salt thereof is about 25 mg.

7. The method according to embodiment 1, wherein the daily dose of N-(3-(6-Amino-5-(2-(N-methylacrylamido)ethoxy)pyrimidin-4-yl)-5-fluoro-2-methylphenyl)-4-cyclopropyl-2-fluorobenzamide, or a pharmaceutically acceptable salt thereof is about 20 mg.

8. The method according to embodiment 1, wherein N-(3-(6-Amino-5-(2-(N-methylacrylamido)ethoxy)pyrimidin-4-yl)-5-fluoro-2-methylphenyl)-4-cyclopropyl-2-fluorobenzamide, or a pharmaceutically acceptable salt thereof, is administered once a day in a dose of about 10 mg, about 35 mg, about 50 mg or about 100 mg.

9. The method according to embodiment 1, wherein N-(3-(6-Amino-5-(2-(N-methylacrylamido)ethoxy)pyrimidin-4-yl)-5-fluoro-2-methylphenyl)-4-cyclopropyl-2-fluorobenzamide, or a pharmaceutically acceptable salt thereof, is administered in a dose of about 10 mg, about 25 mg, about 50 mg or about 100 mg twice daily.

10. The method according to any one of the above embodiments, wherein the subject has moderate to severe SjS.

11. The method according to any one of embodiments 1-10, wherein the subject is selected according to at least one of the following criteria:
a) prior to treatment with compound of Formula (I) or a pharmaceutically acceptable salt thereof, the subject has an ESSPRI score≥5;
b) prior to treatment with the compound of Formula (I) or a pharmaceutically acceptable salt thereof, the subject has an ESSDAI based on weight score≥5 from 8 defined domains selected from biologic, haemetologic, articular, cutaneous, glandular, lymphadenopathy, renal and constitutional.

12. The method according to any one of the above embodiments, wherein the subject is an adult.

13. The method according to any one of the preceding embodiments, wherein said subject achieves by week 12 or by week 24 of treatment at least one of the following:
a) a reduction of the ESSPRI score; and/or
b) a reduction of the ESSDAI score.

14. The method according to any one of the above embodiments, wherein said subject achieves a sustained response as measured by ESSPRI or ESSDAI at week 5 after completion of the treatment.

15. The method according to any one of the above embodiments, wherein N-(3-(6-Amino-5-(2-(N-methylacrylamido)ethoxy)pyrimidin-4-yl)-5-fluoro-2-methylphenyl)-4-cyclopropyl-2-fluorobenzamide, or pharmaceutically acceptable salt thereof is disposed in a pharmaceutical formulation, wherein said pharmaceutical formulation further comprises pharmaceutically acceptable carriers.

16. The method according to any one of embodiments 1-15, wherein N-(3-(6-Amino-5-(2-(N-methylacrylamido)ethoxy)pyrimidin-4-yl)-5-fluoro-2-methylphenyl)-4-cyclopropyl-2-fluorobenzamide, or a pharmaceutically acceptable salt thereof, has a $T_{max}$ of about 0.05-3 hours.

The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural references unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference. The following Examples are presented in order to more fully illustrate the preferred embodiments of the disclosure. These examples should in no way be construed as limiting the scope of the disclosed subject matter, as defined by the appended claims.

Abbreviations

AE adverse event
AUC area under the curve
AUCinf area under the plasma (or serum or blood) concentration-time curve from time zero to infinity (mass×time/volume)
AUClast area under the plasma (or serum or blood) concentration-time curve from time zero to time of last quantifiable concentration (mass×time/volume)
AUCtau area under the plasma (or serum or blood) concentration-time curve from time zero to the end of the dosing interval tau (mass×time/volume)
BCR B cell receptor
Bid or b.i.d. twice a day (for Latin: "bis in die")
BMI Body Mass Index
BTK Bruton's tyrosine kinase
CBC complete blood count
cm centimeter
CL/F the apparent systemic (or total body) clearance from plasma (or serum or blood) following administration (mass/volume)
CNS central nervous system
CV coefficient of variation
DMARDs disease-modifying antirheumatic drugs
ECG Electrocardiogram
eGFR estimated glomerular filtration rate
ELISA Enzyme-linked immunosorbent assay
EMG electromyography
EQ-5D EuroQual 5 dimensions (Standard instrument to measure the health-related quality of life)
ESSDAI EULAR Sjögren's Syndrome Disease Activity Index
ESSPRI EULAR Sjögren's Syndrome Patient Reported Index
EULAR European League against Rheumatism
FACIT-F Functional Assessment of Chronic Illness Therapy-Fatigue
FIH First in Human
h hour
HRCT high resolution computer tomography
i.v. intravenous
IA Interim analysis
INR International Normalized Ratio
kg kilogram
LC-MS/MS liquid chromatography/mass spectrometry-mass spectrometry
mAb monoclonal antibody
MCP-Mod Multiple Comparison Procedure-Modelling
MMRM Mixed effect Model Repeat Measurement
MRT mean residence time
NOAC Novel Oral Anti-Coagulant NSAID Nonsteroidal Anti-Inflammatory Drug
PD Pharmacodynamic(s)
PhGA Physician global assessment scale
PK Pharmacokinetic(s)
PNS peripheral nervous system
PT prothrombin time
PTT partial thromboplastin time
Qd or q.d. once a day (for Latin "quaque die")
QTcF QT interval corrected by Fridericia's formula
Racc Ratio of accumulation of drug
SAE serious adverse event
SjS Sjögren's Syndrome
SOM Site Operations Manual
SPT skin prick test
SS Safety Set
TEC tyrosine-protein kinase
Vz/F the apparent volume of distribution during the terminal elimination phase following administration (volume)

Example 1: Preclinical Studies

Example 1a: BTK Occupancy and Preclinical PK/PD Relationship

The in vivo PD effects of an irreversible BTK inhibitor like compound (I) are determined by the extent and duration of covalent BTK occupancy by the inhibitor. BTK occupancy after treatment with Compound of Formula (I) (also referenced to as Compound (I)) was measured in an ex vivo immunoassay. The fraction of unoccupied BTK protein was assayed after in vitro incubation with a covalent biotinylated BTK probe, since compound (I) and the probe bind to BTK in a mutually exclusive manner. Unoccupied BTK, as well as total BTK relative protein levels were determined in lysates of selected tissues and levels of unoccupied BTK were normalized to total BTK protein levels in the same samples.

In female rats a single oral dose of 3 mg/kg compound (I) resulted in full spleen BTK occupancy, a dose of 1 mg/kg resulted in 76%-81% occupancy, whereas after a single dose of 0.3 mg/kg only partial occupancy of 30% was reached. BTK occupancy in blood reached levels consistent with those observed in spleen. From the experimental data it was apparent that a short transient systemic exposure of compound (I) is sufficient to achieve full BTK occupancy in several tissues at low oral doses of 1-3 mg/kg. The blood exposure of compound (I) after a 1 mg/kg dose reached 49.1 nM at 0.5 hours and was 5.6 nM at 5 hours post dose. This very low and transient systemic exposure is consistent with the PK/PD model typical of irreversible inhibitors.

The duration of BTK occupancy was determined in rats and mice after single oral dose of compound (I) for spleen, blood, lymph nodes and lung. In rats, BTK occupancy showed a long half-life in blood of approximately 87 hours. The estimated BTK occupancy half-life in rat spleen is significantly shorter than in blood with only approximately 5 hours. The different turnover rates may reflect the fact that BTK expressing B cells and monocytes in peripheral blood are resting and metabolically relatively inactive compared to the spleen. The longer persistence of BTK occupancy in blood has been reported before (Advani et al 2013, J Clin Onc; 31(1):88-94). All other tissues analyzed (lung and lymph node) showed a similar BTK turnover and occupancy half-life as spleen.

As the levels of BTK-expressing cells in skin were too low to allow occupancy measurement, the duration of the PD effect in skin after single dose was assessed in the reverse passive Arthus (RPA) model of mast cell FcγRIII-mediated inflammation. In this model, the inhibition of skin swelling was maximal when compound (I) was dosed 2 hours prior to eliciting the Arthus reaction. The effect diminished gradually and reached baseline when the Arthus reaction was triggered 45 hours or later after compound (I) dosing. This suggests that BTK occupancy in the skin shows a similar time course like spleen, lung and lymph nodes.

In these preclinical pharmacology studies, the BTK occupancy and the respective pharmacologic readouts showed a strong correlation. Thus, BTK occupancy is a suitable PD biomarker for use in clinical studies and therefore was used in Phase 1 clinical studies.

Example 2: Phase 1 Clinical Trial

A first-in-human study was conducted to assess the safety and tolerability, pharmacokinetics (PK) and pharmacodynamics (PD) of single and multiple doses of compound (I) both as once daily (qd) and twice daily (bid) oral administration in healthy volunteers and those with atopic diathesis, to support further clinical development of compound (I) in autoimmune diseases. This study also explored the effect of food intake.

First-in-human study in up to approximately 168 healthy volunteers (HVs), of which 64 (in Parts 2 & 4) had asymptomatic atopic diathesis.

Part 1 was a double-blind (subject and investigator blind, sponsor unblinded), placebo-controlled single ascending dose (SAD) escalation study of 10 cohorts (N=80)

Part 2 was a double-blind (subject and investigator blind, sponsor unblinded), placebo-controlled multiple ascending dose (MAD) (13 doses over 12 days) escalation study employing once daily dosing in 6 cohorts in healthy volunteers with asymptomatic atopic diathesis (N=48)

Part 3 was a single dose open-label crossover food effect study in 12 HVs

Part 4 was a double-blind (subject and investigator blind, sponsor unblinded), placebo-controlled multiple dose (25 doses over 12 days) study employing twice daily dosing in 2 cohorts of healthy volunteers with asymptomatic atopic diathesis (N=16)

The SAD part (Part 1) had ten dose levels and the MAD parts (Parts 2 & 4) consisted of eight dose levels (6 cohorts using single daily dosing in Part 2 and 2 cohorts using twice daily dosing in Part 4). Eight subjects were randomized into each cohort to receive either compound (I) or matching placebo in a 6:2 (active: placebo) ratio in the SAD and MAD parts. Within the SAD part, doses up to approximately 4 times the estimated pharmacologically active dose (PAD) were to be evaluated before the MAD part of the study was started, providing there was no safety signal emerging from the SAD part until then. The total daily dose of compound (I) used in Part 2 (MAD qd regimen) and Part 4 (Multiple dose bid regimen) did not exceed the highest SAD dose level explored. Moreover, the total daily dose of Part 4 did not exceed the total daily dose of Part 2.

In Part 1 (SAD) sentinel dosing was to take place for the first administration at each dose level as follows. The first two subjects were dosed on the first day (one with active drug, one with placebo). After a 48-hour observation period the remaining 6 subjects of the cohort (five with active drug, one with placebo) were dosed.

Standard safety monitoring was used throughout all study parts. A dedicated assessment of potential skin bruising events were included. All vital signs, physical examination and subject history, ECGs, adverse events, and laboratory safety parameters (blood chemistry, hematology and urinalysis) up to 96 hours post last dose as well as PK data from the previous dose group (if available) up to 48 hours post last dose were to be reviewed in a blinded fashion for each cohort before dose escalation. Summary safety reports of reported adverse events, clinical safety laboratory parameters, QTc and heart rate were provided after completion of each dose level.

In Parts 1, 2 and 4, each subject participated in a 28-day Screening period (Days −29 to −2), a Baseline period, a Treatment period and a Follow-up period that included an End-of-Study evaluation.

In Part 1, subjects were admitted to the study site on Day −2 or −1 for baseline safety assessments and to confirm eligibility. Eligible subjects received a single dose of compound (I) or placebo under fasting conditions on Day 1. They were domiciled from Day −1 to the morning of Day 5 (96 hours post last drug administration).

In Parts 2 and 4, subjects were admitted on Day −2 or −1 for baseline safety assessments and to confirm eligibility. Eligible subjects received the first dose of compound (I) under fasting conditions on Day 1, and continued to take study medication under fasting conditions up to and including Day 12. Subjects were domiciled from Day −2 or −1 until the morning of Day 16, which equals 96 hours after the last dose of compound (I) was received. In Parts 2 and 4, the study medication was given once daily and twice daily respectively (details are found in the schedule of assessments).

Part 3 was an open-label, randomized, two-way cross-over, single dose study to assess food effects. In Part 3, each subject participated in a 28 day screening period (Day −29 to −2), 2 baseline (Day −1) and 2 treatment periods, each consisting of a single dose administration on Day 1 followed by safety and PK assessment up to Day 5. Treatment period 2 consisted of a follow-up visit and an end of study evaluation on Day 22 and 40, respectively. The two treatment periods were separated by a wash-out period of at least 18 days (+/−1 day).

| Primary objective(s) | |
|---|---|
| Objective | Endpoint |
| All Parts: To assess the safety and tolerability of single and multiple ascending oral doses of compound (I) | All safety assessments including physical examination and anamnesis, vital signs, ECG, safety laboratory, AEs, and SAEs. Included a designated evaluation of the occurrence of skin bruising. |

| Secondary objectives | |
|---|---|
| Objective | Endpoint |
| Parts 1 2 & 4: to assess the blood PK of single and multiple doses of compound (I) in healthy volunteers and atopic subjects. | Single and multiple dose PK parameters such as Cmax, Tmax, AUCinf, AUClast, AUCtau, T½, MRT, Racc, Vz/F and Cl/F. |
| Part 3: to assess the blood PK of a single dose of compound (I) under fed and fasted conditions in healthy volunteers. | Single dose PK parameters: Cmax, Tmax, AUClast, AUCinf, T½, MRT, Vz/F and CL/F. |

| Exploratory objectives | |
|---|---|
| Objective | Endpoint |
| Parts 1, 2 & 4: to explore urine PK (Part 2 & 4) and PD of single and multiple doses of compound (I). | BTK occupancy in peripheral blood Skin prick test responses to a known allergen (Part 2 & 4) ex vivo cellular PD biomarkers that provided additional measures of drug response to compound (I) by inhibition of peripheral blood basophil degranulation (FcεR-induced CD63 and CD203c expression) |
| All Parts: to describe the concentration effect relationship with PD markers (e.g. BTK occupancy, ex vivo cellular PD biomarkers) and characterize nonlinearities in PK (if any) using population PK-PD models | Population model PK parameters (e.g., CL/F, V/F and Ka) and PD model parameters (e.g., irreversible binding constant Kirr) and their associated intra and inter-individual variability (CV %) |

Inclusion Criteria

1. Male and female healthy subjects with an age range between 18 and 65 years (inclusive), and in good health as determined by past medical history, physical examination, vital signs, electrocardiogram, and laboratory tests at screening. Healthy subjects participated in Part 2 or Part 4 with atopic diathesis as per eligibility for these specific study portions. Atopic healthy volunteers had to have a positive skin prick test to a known allergen at screening (atopic diathesis) but were clinically asymptomatic and did not require any systemic medication.
2. Subjects were required to weigh at least 50 kg with a body mass index (BMI) within the range of 18-30 kg/m2 (inclusive). BMI=body weight (kg)/[Height (m)]$^2$.
3. At screening, and first baseline, vital signs (body temperature, systolic and diastolic blood pressure and pulse rate) were assessed in the sitting position after the subject has rested for at least 3 minutes and again (when required) after 3 minutes in the standing position. Sitting vital signs were required to be within the following ranges (inclusive):
Oral body temperature between 35.0-37.5° C.
Systolic blood pressure 90-139 mm Hg
Diastolic blood pressure 50-89 mm Hg
Pulse rate 50-90 bpm Key Exclusion Criteria 1. History of hypersensitivity to any of the study drugs or to drugs of similar chemical classes.
2. History of clinically significant ECG abnormalities, or any of the following ECG abnormalities at screening and/or pre-treatment:
PR interval>200 msec
QRS complex>120 msec
QTcF>450 msec (males)
QTcF>460 msec (females)

3. Hemoglobin levels below 12.0 g/dL at screening or first baseline.
4. Platelet count outside of the normal range (below $150 \times 10^9$/L or above $450 \times 10^9$) at screening or first baseline.
5. Any clinically significant abnormalities in any of the standard coagulation tests including the prothrombin time (PT), partial thromboplastin time (PTT), or International Normalized Ratio (INR) at screening and/or baseline.
6. History or presence of thrombotic or thromboembolic event, or increased risk for thrombotic or thromboembolic event.

Treatments Administered

Part 1 (SAD)

Subjects were assigned to one of the following 10 cohorts. In each cohort, 8 subjects were randomized to either compound (I) or matching placebo in an overall 6:2 ratio. The first sub-cohort was randomized in a 1:1 ratio as one subject on compound (I) and one on matching placebo. The remaining 6 subjects per cohort, dosed after a 48-hour observation period of the initially dosed 2 subjects, were randomized in a 5:1 ratio.
Cohort 1: single oral dose of 0.5 mg compound (I) or matching placebo
Cohort 2: single oral dose of 1.5 mg compound (I) or matching placebo
Cohort 3: single oral dose of 5 mg compound (I) or matching placebo
Cohort 4: single oral dose of 15 mg compound (I) or matching placebo
Cohort 5: single oral dose of 30 mg compound (I) or matching placebo
Cohort 6: single oral dose of 60 mg compound (I) or matching placebo
Cohort 7: single oral dose of 100 mg compound (I) or matching placebo
Cohort 8: single oral dose of 200 mg compound (I) or matching placebo
Cohort 9: single oral dose of 400 mg compound (I) or matching placebo
Cohort 10: single oral dose of 600 mg compound (I) or matching placebo Part 2 (MAD, qd Regimen)

Subjects were assigned to one of the following 6 cohorts. In each cohort, 8 subjects were randomized to either compound (I) or matching placebo in a 6:2 ratio.
Cohort 1: multiple oral doses of 10 mg compound (I) or matching placebo
Cohort 2: multiple oral doses of 25 mg compound (I) or matching placebo
Cohort 3: multiple oral doses of 50 mg compound (I) or matching placebo
Cohort 4: multiple oral doses of 100 mg compound (I) or matching placebo
Cohort 5: multiple oral doses of 400 mg compound (I) or matching placebo
Cohort 6: multiple oral doses of up to 600 mg compound (I) or matching placebo Part 3 (Food Effect)

Subjects were randomized to one of the 2 treatment sequences in the ratio of 1:1:

| Sequence | Period 1 | Period 2 |
| --- | --- | --- |
| 1 | Compound (I) (60 mg) Fasted | Compound (I) (60 mg) Fed |
| 2 | Compound (I) (60 mg) Fed | Compound (I) (60 mg) Fasted |

Part 4 (MAD, bid Regimen)

Subjects were assigned to one of the following cohorts. In each cohort, 8 subjects were randomized to either Compound (I) or matching placebo in a 6:2 ratio.
Cohort 1: multiple oral doses of 100 mg Compound (I) or matching placebo in a bid regimen
Cohort 2: multiple oral doses of 200 mg Compound (I) or matching placebo in a bid regimen Pharmacokinetics Data Bioanalytical Methods Pharmacokinetic samples were obtained in blood and evaluated in all subjects at all dose levels. The samples from placebo subjects were not analyzed. The samples for PK assessments from subjects were collected at time points defined in the study. Compound (I) concentrations were determined in blood by a validated LC-MS/MS method.

Single Ascending Doses of 0.5 mg-600 mg Pharmacokinetics

Mean blood concentration-time course of compound (I) after single ascending doses are shown in FIG. 1.

Compound (I) was rapidly absorbed with time to reach C max of about 1-1.5 hr across all doses. The absorption phase was characterized by a single distinct absorption peak in most subjects. Drug disposition displayed a bi-exponential decline. Most of the drug was eliminated under the initial distribution phase suggesting substantial drug clearance may occur prior to reaching whole-body tissue equilibrium. The apparent terminal elimination phase was not reached until 12 hours post dose and was measurable only in subjects receiving doses of 100 mg and above. Measureable terminal half-lives ranged from 4 hr (100 mg) up to 18 hr (600 mg) leading to a mean residence time (MRT) in the circulation of 1 h up to 5 hours (MRT≈T1/2/ln2). The distribution phase demonstrated a dominant dose-independent T1/2 of ~1 h. The calculated geometric mean of oral blood clearance after single dose administration (CL/F) ranged from 250 to 506 L/h across SAD cohorts, with an estimate of about 383 L/h across all cohorts.

Multiple Oral Dose Pharmacokinetics

Figure 2:
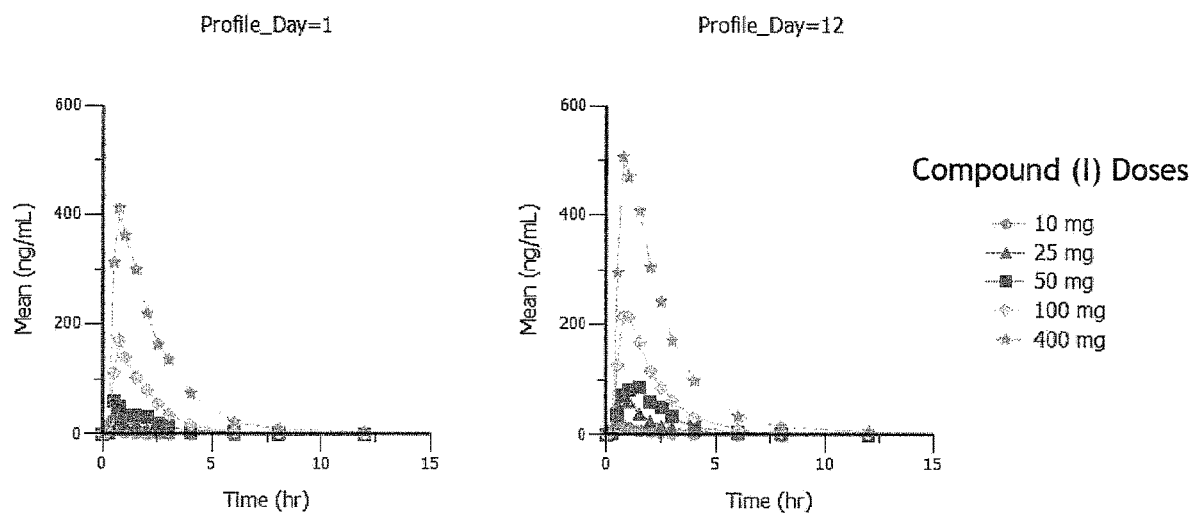
FIG. 2: Blood concentration—time course of compound (I) after multiple ascending doses of 10 mg-400 mg, q.d. dosing

Mean blood concentration-time course of compound (I) after multiple ascending doses of 10 mg-400 mg are shown in FIG. 2.

Geometric mean apparent clearance at steady-state after oral dosing (CLss/F, Day 12 MAD, q.d.) ranged between 246 L/h to 414 L/h across cohorts. In general a lower clearance was observed at steady state when compared to day 1 but this difference almost disappeared at doses of 100 mg and above (Table 2-1 (day 1) and Table 2-2 (day 12)). The reason for this behavior is likely the covalent target (BTK) binding contributing to the initial clearance of compound (I). This effect is most prominant at day 1 as on consecutive days the remaining target occupancy at trough reduces the fractional contribution of target binding to the clearance (CLss/F). Naturally, this difference decreases with increase in the dose when target occupancy at trough is near complete. Consequently, drug exposure (AUC, C max) was found to be higher on day 12 compared to day 1, as illustrated by the (within-subject) drug accumulation ratio (Racc), which ranged between 5 (low dose) to 1.2 (high dose) and was generally higher for AUC than C max, confirming that an effect on systemic clearance may be involved.

TABLE 2-1

Summary of PK parameters of compound (I) at multiple ascending doses of 10-600 mg, q.d. dosing
Analyte: compound of Formula (I) , Matrix: Blood and Urine
Profile: Day 1

| PK parameter (unit) | Compound of Formula (I) | | | | | |
|---|---|---|---|---|---|---|
| | 10 mg qd N = 6 | 25 mg qd N = 6 | 50 mg qd N = 6 | 100 mg qd N = 6 | 400 mg qd N = 6 | 600 mg qd N = 6 |
| Cmax (ng/mL) | 8.40 ± 2.02 (24.1) 8.03 (6.36-11.4) [6] | 40.9 ± 21.6 (52.9) 37.3 (14.1-80.4) [6] | 76.5 ± 22.0 (28.8) 70.1 (47.3-107) [6] | 187 ± 85.0 (45.4) 189 (75.6-285) [6] | 518 ± 89.1 (17.2) 513 (383-622) [6] | 550 ± 87.6 (15.9) 545 (461-691) [6] |
| Tmax (h) | 0.517 (0.500-1.00) [6] | 0.875 (0.283-1.50) [6] | 0.500 (0.483-2.00) [6] | 0.742 (0.500-1.95) [6] | 0.750 (0.500-1.50) [6] | 0.750 (0.500-3.00) [6] |
| AUClast (h*ng/mL) | 4.17 ± 1.38 (33.0) 4.40 (1.79-5.62) [6] | 43.9 ± 24.6 (56.2) 45.5 (15.3-78.5) [6] | 113 ± 34.2 (30.3) 103 (81.9-154) [6] | 311 ± 89.1 (28.6) 333 (168-416) [6] | 973 ± 379 (39.0) 826 (694-1720) [6] | 1080 ± 377 (35.1) 931 (699-1700) [6] |
| AUC0-24 (h*ng/mL) | 4.94 ± 1.35 (27.2) 4.94 (3.99-5.89) [2] | 44.9 ± 25.2 (56.0) 46.6 (15.6-79.7) [6] | 116 ± 32.9 (28.4) 107 (84.0-155) [6] | 315 ± 91.5 (29.0) 338 (168-419) [6] | 977 ± 378 (38.7) 826 (702-1720) [6] | 1080 ± 377 (35.0) 932 (700-1700) [6] |
| MRT (h) | 0.761 ± 0.151 (19.8) 0.766 (0.548-0.956) [6] | 1.18 ± 0.490 (41.6) 1.17 (0.460-1.87) [6] | 2.53 ± 1.17 (46.4) 2.44 (1.17-4.65) [6] | 2.79 ± 1.28 (45.7) 2.16 (1.65-4.62) [6] | 3.02 ± 1.11 (36.8) 2.94 (1.64-4.98) [6] | 3.14 ± 0.580 (18.5) 3.22 (2.31-3.96) [6] |

Statistics are Mean ± SD (CV %)
Median (Min-Max) [n]
CV % = Coefficient of variation (%) = SD/Mean*100
For Tmax and T½, only Median (Min-Max) [n] are presented

TABLE 2-2

Analyte: Compound of Formula (I), Matrix: Blood and Urine
Profile: Day 12

| PK parameter (unit) | Compound of Formula (I) | | | | | |
|---|---|---|---|---|---|---|
| | 10 mg qd N = 6 | 25 mg qd N = 6 | 50 mg qd N = 6 | 100 mg qd N = 6 | 400 mg qd N = 6 | 600 mg qd N = 6 |
| Cmax (ng/mL) | 18.2 ± 5.90 (32.4) 17.2 (11.8-26.4) [6] | 85.9 ± 31.5 (36.6) 78.4 (43.9-126) [6] | 102 ± 22.0 (21.6) 100 (73.3-131) [6] | 233 ± 84.1 (36.1) 205 (167-386) [6] | 551 ± 263 (47.7) 476 (260-928) [6] | 563 ± 229 (40.6) 475 (377-985) [6] |
| Tmax (h) | 0.625 (0.500-1.00) [6] | 0.750 (0.500-1.00) [6] | 1.00 (0.533-1.50) [6] | 0.867 (0.733-1.50) [6] | 0.758 (0.700-1.50) [6] | 0.883 (0.500-3.00) [6] |
| AUClast (h*ng/mL) | 22.9 ± 3.50 (15.3) 22.4 (18.3-28.2) [6] | 114 ± 59.7 (52.2) 98.2 (30.1-190) [6] | 207 ± 80.4 (38.9) 179 (126-323) [6] | 488 ± 172 (35.3) 444 (336-770) [6] | 1300 ± 602 (46.3) 1180 (650-2310) [6] | 1240 ± 341 (27.5) 1070 (953-1740) [6] |
| AUCinf (h*ng/mL) | 24.7 ± 3.65 (14.8) 24.3 (19.6-29.9) [6] | 117 ± 60.4 (51.5) 102 (31.7-194) [6] | 209 ± 80.0 (38.2) 181 (127-325) [6] | 577 ± 207 (35.9) 595 (361-774) [3] | 1330 ± 608 (45.8) 1210 (665-2330) [6] | 1260 ± 338 (26.8) 1090 (994-1760) [6] |
| AUC0-24 (h*ng/mL) | 24.0 ± 3.60 (15.0) 23.6 (18.9-29.3) [6] | 117 ± 60.9 (52.2) 101 (30.9-194) [6] | 209 ± 80.2 (38.4) 181 (127-325) [6] | 485 ± 179 (36.9) 429 (336-774) [6] | 1280 ± 577 (45.3) 1140 (677-2270) [6] | 1230 ± 356 (29.0) 1060 (908-1740) [6] |
| T½ (h) | 0.961 (0.667-1.21) [6] | 1.15 (0.680-1.33) [6] | 1.15 (0.813-1.55) [6] | 1.41 (1.41-11.9) [3] | 8.51 (1.22-22.3) [6] | 8.29 (4.69-17.3) [6] |

TABLE 2-2-continued

Analyte: Compound of Formula (I), Matrix: Blood and Urine
Profile: Day 12

| PK parameter (unit) | Compound of Formula (I) | | | | | |
|---|---|---|---|---|---|---|
| | 10 mg qd N = 6 | 25 mg qd N = 6 | 50 mg qd N = 6 | 100 mg qd N = 6 | 400 mg qd N = 6 | 600 mg qd N = 6 |
| Vss/F (L) | 554 ± 90.4 (16.3) 562 (407-657) [6] | 407 ± 208 (51.1) 334 (247-793) [6] | 431 ± 172 (40.0) 346 (313-751) [6] | 1910 ± 2780 (145.9) 338 (264-5120) [3] | 4400 ± 3340 (75.8) 3440 (624-8820) [6] | 7130 ± 5120 (71.9) 7070 (2340-16500) [6] |
| CLss/F (L/h) | 425 ± 64.8 (15.3) 423 (341-529) [6] | 307 ± 253 (82.5) 248 (129-809) [6] | 268 ± 92.8 (34.6) 276 (154-395) [6] | 198 ± 88.7 (44.8) 166 (129-298) [3] | 366 ± 150 (41.0) 351 (177-591) [6] | 521 ± 131 (25.1) 569 (345-661) [6] |
| $T^{1/2}$, acc | 1.00 (1.00-1.00) [6] | 1.00 (1.00-1.00) [6] | 1.00 (1.00-1.00) [6] | 1.01 (1.00-1.73) [6] | 1.18 (1.00-1.90) [6] | 1.16 (1.03-1.62) [6] |
| Amount recovered (mg) | 0.0663 ± 0.0309 (46.5) 0.0630 (0.0346-0.109) [6] | 0.114 ± 0.0706 (62.0) 0.126 (0.0326-0.217) [6] | 0.233 ± 0.0880 (37.7) 0.185 (0.165-0.378) [5] | 0.648 ± 0.330 (50.9) 0.561 (0.305-1.12) [6] | 1.25 ± 0.647 (51.7) 1.12 (0.547-2.37) [6] | 1.54 ± 0.915 (59.3) 1.43 (0.528-3.03) [6] |
| Amount recovered (%) | 0.663 ± 0.309 (46.5) 0.630 (0.346-1.09) [6] | 0.456 ± 0.283 (62.0) 0.502 (0.130-0.868) [6] | 0.467 ± 0.176 (37.7) 0.370 (0.331-0.757) [5] | 0.648 ± 0.330 (50.9) 0.561 (0.305-1.12) [6] | 0.313 ± 0.162 (51.7) 0.280 (0.137-0.593) [6] | 0.257 ± 0.153 (59.3) 0.238 (0.0880-0.506) [6] |
| Renal clearance (mL/min) | 45.3 ± 18.0 (39.8) 41.6 (24.4-70.3) [6] | 16.8 ± 6.81 (40.5) 18.9 (5.43-24.3) [6] | 20.4 ± 2.40 (11.7) 20.5 (17.1-23.4) [5] | 21.6 ± 5.41 (25.1) 21.1 (14.6-30.9) [6] | 16.9 ± 7.13 (42.3) 14.5 (11.5-30.7) [6] | 20.0 ± 8.25 (41.2) 18.1 (8.98-30.3) [6] |

Statistics are Mean ± SD (CV %)
Median (Min-Max) [n]
CV % = Coefficient of variation (%) = SD/Mean*100
For Tmax and $T^{1/2}$, only Median (Min-Max) [n] are presented In general, blood concentrations at 24 hours post last dose were typically below 1 ng/ml, except for a few subjects at 100 mg and above indicating near-complete washout of compound (I) within two consecutive doses. The latter also suggests that steady state is reached within a few doses.

Figure 3:
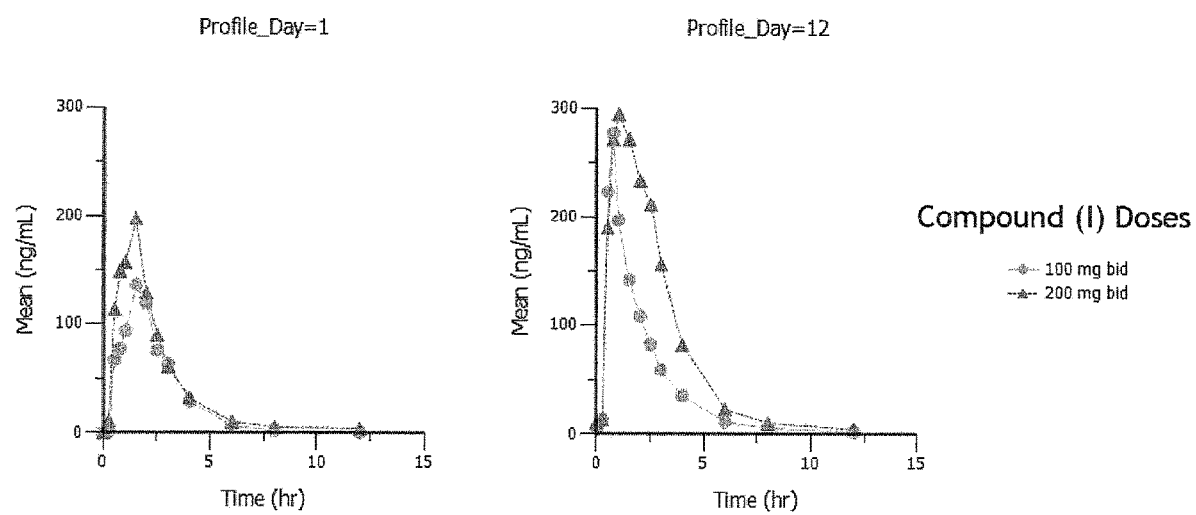
FIG. 3: Blood concentration—time course of compound (I) after multiple ascending doses of 100 mg b.i.d. and 200 mg b.i.d.

Due to the higher turnover of BTK in tissues, b.i.d. dosing was also investigated. Mean blood concentration time profiles obtained after multiple ascending twice daily doses of 100 mg and 200 mg are shown in FIG. 3. In line with results from other cohorts, a fast absorption with a T max of around 1 h was observed for doses after b.i.d. regimen. The observed accumulation factor (Racc) amounted to 1.5 (100 mg) and 2.0 (200 mg) for AUC and about 1.65 for C max (both doses). A dose proportional increase of AUCtau was observed at day 12 while only slight increase (1.33-fold) was found for C max. In conclusion, b.i.d dosing of compound (I) provides an option to address the faster target resynthesis in tissues during the dosing interval without compromising the overall PK profile and the need for high dose q.d. treatment.

Food Effect: Result Part 3

Figure 4:
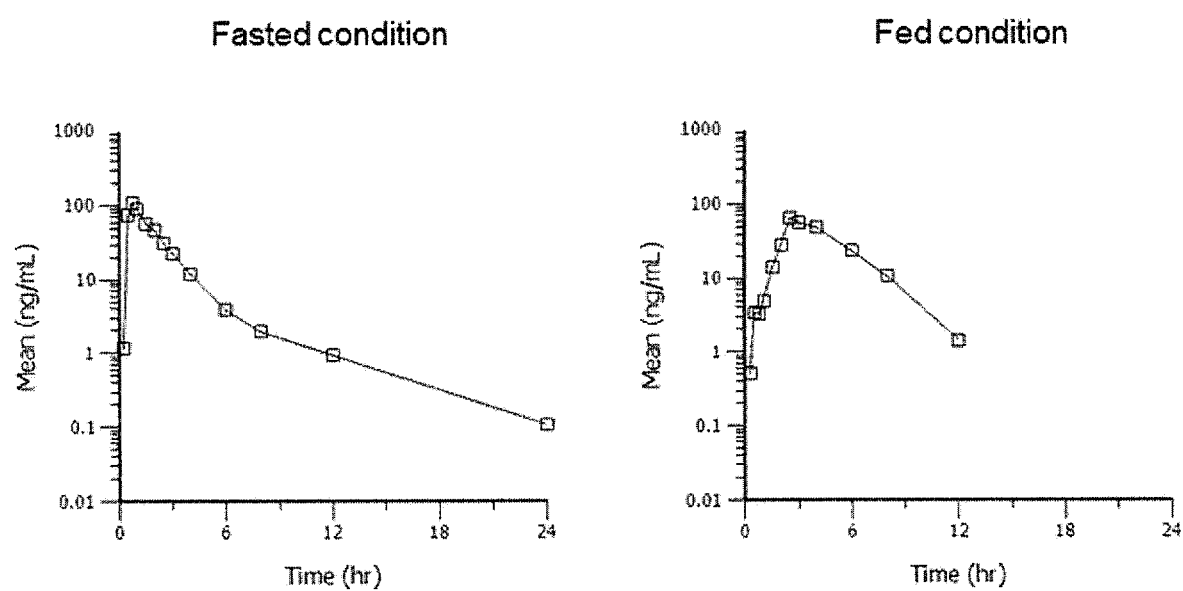
FIG. 4: Food effect as observed after a single oral dose of 60 mg of compound of Formula (I)

The PK data from the food effect cohort summarized in Table 2-3 below indicated a lower absorption rate as suggested by a 1.25-fold lower C max and a more complete overall absorption as indicated by a 1.4-fold higher AUC0-24. Most importantly the mean T max was shifted from 1 hr (fasted) to >3 hr (fed). (FIG. 4)

TABLE 2-3

Summary of PK parameters: Food effect compound (I) after a single dose of 60 mg

| Condition | Variable | Mean | SD | Min | Max | Geomean | CV % Geomean |
|---|---|---|---|---|---|---|---|
| FAST | AUC0-24 | 202.29 | 94.28 | 70.40 | 407.26 | 182.08 | 51.66 |
| | AUClast | 196.49 | 91.45 | 69.21 | 399.64 | 177.17 | 52.01 |
| | Cmax | 114.81 | 57.97 | 33.90 | 252.00 | 100.95 | 60.40 |
| | Tlast | 10.50 | 4.98 | 6.00 | 24.00 | 9.66 | 42.80 |
| | Tmax | 1.02 | 0.47 | 0.75 | 2.00 | 0.95 | 38.32 |
| FED | AUC0-24 | 263.89 | 91.56 | 132.79 | 426.96 | 248.51 | 38.46 |
| | AUClast | 251.96 | 85.43 | 130.60 | 396.42 | 237.84 | 37.69 |
| | Cmax | 83.39 | 21.41 | 52.10 | 126.00 | 80.86 | 26.64 |
| | Tlast | 9.50 | 2.28 | 6.00 | 12.00 | 9.25 | 24.72 |
| | Tmax | 3.42 | 1.41 | 2.00 | 6.00 | 3.18 | 39.95 |

Units: ADC (ng*hr/mL); Cmax(ng/mL); T (hr)

CV (Coefficient variation (%) = SD/Mean*100

Pharmacodynamics

Pharmacodynamics (PD) was characterized by assessing target occupancy and distal pathway inhibition. Measurements of BTK occupancy in human whole blood (derived as ratio of free and total BTK), served as direct marker of therapeutic target engagement.

The relationship between BTK occupancy, dose, systemic compound exposure and efficacy on complex in vivo pathway and disease readouts has been established across preclinical models for compound of Formula (I). (e.g. Example 1)

Compound of formula (I) is an irreversible inhibitor of BTK, the extent and duration of BTK occupancy were determined. The PD effect of compound (I) was assessed by measuring both free BTK (not bound) and total BTK in whole blood by enzyme-linked immunosorbent assay (ELISA) on Meso Scale Diagnostics (MSD) platform in two separate assays.

The relationship between dose and pharmacodynamics was characterized by measurements of BTK occupancy in human blood (derived as ratio of free and total BTK), a direct marker of therapeutic target engagement. BTK occupancy was determined for single ascending doses ranging 0.5 to 400 mg, for q.d. multiple ascending doses ranging from of 10 mg and 400 mg, and for b.i.d. multiple ascending doses of 100 mg and 200 mg.

Compound of Formula (I) exhibited a clear dose-dependent increase in both extent and duration of peripheral blood BTK occupancy. Peak target occupancy was generally seen as early as 0.5 h post dose, indicating rapid onset with no relevant hysteresis in drug effect relative to peak drug exposure. As concluded from its ability to bind BTK covalently, target occupancy was sustained well beyond its disposition from the systemic circulation, indicating a non-equilibrium PK-PD relationship. Accordingly, duration of BTK occupancy is concluded to be governed by the rate of de novo synthesis of BTK.

Figure 5:
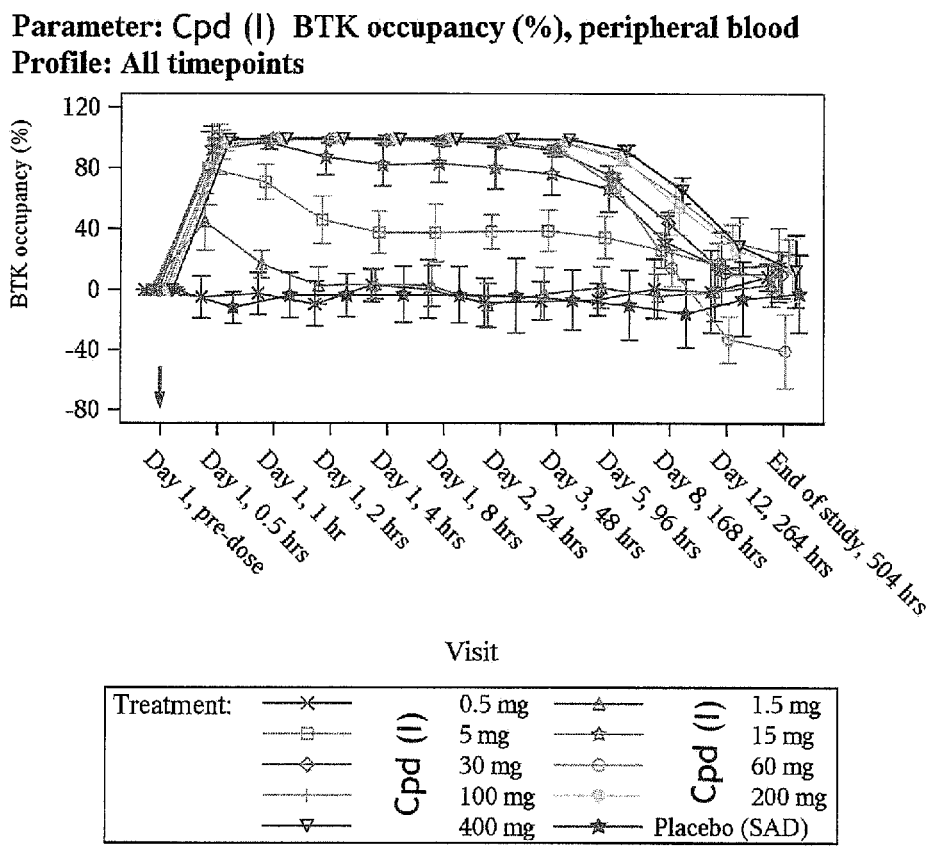
FIG. 5: Arithmetic mean (SD) percent BTK occupancy in peripheral blood after a single dose of Compound of Formula (I)

Unlike the lower dose cohorts (0.5-1.5 mg), single doses of 15 mg compound (I) and above established a peak target occupancy approaching 100% in nearly all subjects, which remained above 80% at 24 h. While the response varied greatly among subjects at 15 mg, doses of 30 mg and higher conveyed sustained (>24 h) and near-complete (>90%) occupancy in all subjects, with clearly reduced between-subject variability. Time to refresh BTK protein pool to pre-dose levels was about 10 days, corresponding to median turnover T1/2 of about 48 hours (FIG. 5).

After multiple doses of compound (I), already 10 mg compound (I) q.d achieved >96% through BTK occupancy in blood pre-dose at day 12.

In addition, ex vivo inhibition of basophil activation (monitored by surface expression of CD63 and CD203c) was used as distal mechanistic biomarker to test downstream PD effects of compound (I). To determine the PD effect of compound (I) on basophil activation, whole blood was stimulated ex vivo with anti-IgE. Degranulation was evaluated by percentage of CD63+ and CD203+ basophils by flow cytometry.

After single ascending doses of compound (I), data indicate a dose-dependent inhibition of FcεR1-mediated basophil activation. Ex-vivo blood basophil activation as measured by CD63 was near-completely inhibited (>89%) at doses of 60 mg and reached close to a 100% inhibition at higher doses 24 h post dose. In contrast, maximum inhibition of CD203c 24 h after a single dose of compound (I) (appr. 50% inhibition) was only achieved with 200 mg compound (I).

Figure 6:
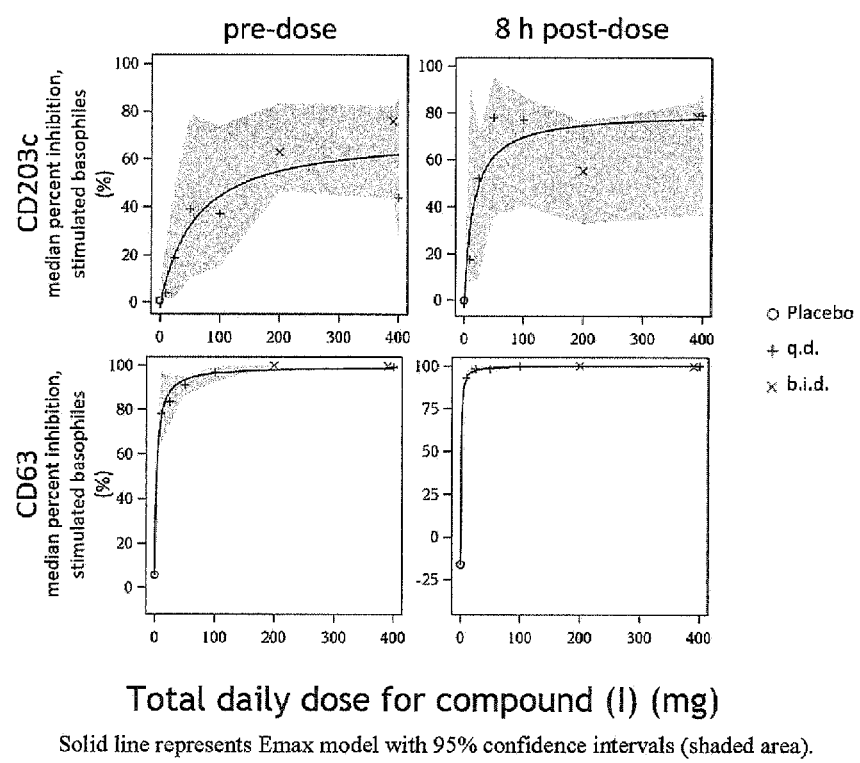
FIG. 6: Median percent inhibition of basophil activation versus total daily dose of Compound of Formula (I) at day 12 of multiple ascending doses of Compound of Formula (I)

At day 12, 8 h after q.d. or b.i.d. administration of MAD of compound of Formula (I), already the lowest tested dose of compound (I) (10 mg q.d.) resulted in >90% inhibition of CD63 upregulation and trough level inhibition of CD63 is >90% at compound (I) doses≥50 mg q.d. (FIG. 6). Maximum trough inhibition of CD203c activation at Day 12 was consistently higher than after a single dose of compound (I) and was only achieved with b.i.d. administration of 100 mg and 200 mg compound (I).

The ability of compound (I) to inhibit a defined allergen response has been evaluated by means of the skin prick test (SPT) in healthy atopic subjects in the MAD study part of the first in human study. SPT was performed prior to dosing (at screening, baseline and pre-dose on Day 1) and at different time points after the first dose (Day 1) and after 11 days of once daily dosing (Day 12).

Figure 7:
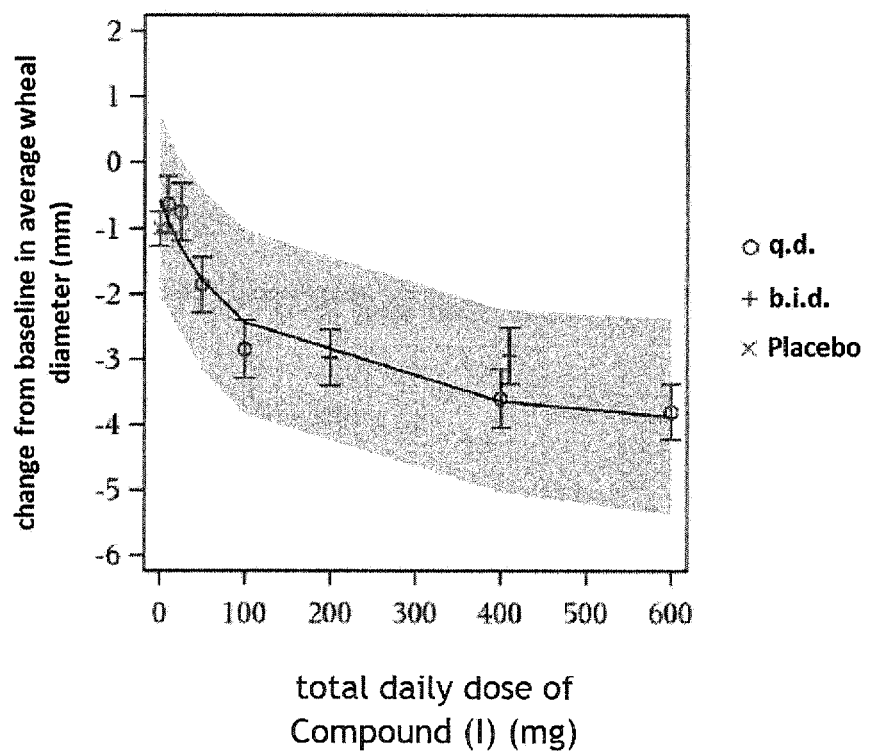
FIG. 7: Reduction of whealsize in skin prick test in multiple ascending dose

Similar to the inhibition of ex vivo basophil activation, a dose-dependent effect on wheal diameter was discernable in multiple ascending dose cohorts as indicated by the reduction of average post-dose wheal size compared to baseline (FIG. 7). The effect started to plateau at around 100 mg compound (I) q.d.

Rationale for Dose Selection/Conclusion

Healthy volunteers have been exposed to compound (I) in phase 1 clinical studies with doses ranged from 0.5 mg to 600 mg either given as a single dose or given up to 18 days once or twice daily. Compound (I) was well tolerated and there was no serious or severe adverse event related to compound (I) intake. In the clinical study, observed adverse events (AEs) did not appear to be dose-dependent, the majority were single events, and were generally mild in nature. Thus, clinical safety information support the doses selected for this Phase 2b study.

The dose-levels of this invention were derived from the following analyses (BTK occupancy, inhibition of basophil activation (monitored by CD63 and CD203c up-regulation) in healthy volunteers; and impact on skin prick tests (SPT) in asymptomatic atopic healthy volunteers—a proxy for mast cell and basophil inhibition within the skin.

In this above described clinical trial, administration of 10 mg of compound (I) q.d. resulted in nearly complete BTK occupancy in blood, >90% reduction of CD63 up-regulation (8 h after administration of COMPOUND (I) in steady state), and minimal inhibition of wheal size in SPT. 10 mg of compound (I) q.d. therefore corresponds to the onset of biological activity. At 100 mg of compound of Formula (I), mean reduction of wheal size in SPT started to plateau. Therefore, 100 mg of the compound corresponds to the maximal effect of COMPOUND (I). A middle dose of thirty-five mg compound (I) q.d. is well suited to accurately describe the dose-response curve of COMPOUND (I) q.d.

Compound of Formula (I) inhibits BTK by covalent binding. While BTK occupancy in blood is >24 hours (h), fast BTK turnover in tissue (example given approximately 5 hours in the spleen of rodents) may require b.i.d. administration of compound (I) to reach maximal efficacy. Doses of 10 mg, 25 mg and 100 mg compound (I) b.i.d., respectively, accurately describe the dose-response curves of compound (I) when given twice a day.

Safety in Humans

For the analysis of adverse effects, the Placebo subjects from all SAD and MAD cohorts (2 per cohort) and separated by the SAD and MAD parts were pooled into one Placebo group (n=20 for SAD and n=16 for MAD) to be compared with each single compound (I) dose group (n=6 each) and the total compound (I) group (n=60 for SAD and n=48 for MAD). There were no apparent major differences in the demographic data between placebo and the active groups both for the SAD and MAD populations. Safety assessment of the FIH study in healthy volunteers does not reveal significant safety concerns at dosing up to 600 mg.

Example 3: Efficacy and Safety Data in Subjects with Moderate to Severe SjS

A Phase 2 study is conducted with the Compound of Formula (I) designed to establish safety and efficacy and characterize the dose-response of Compound of Formula (I) in subjects with moderate to severe SjS to allow further development of the compound for treatment of this disease.

| Protocol summary | |
|---|---|
| Brief title | A Phase 2 study to evaluate the safety and efficacy of Compound of Formula (I), in patients with Sjögren's Syndrome (SjS) |
| Study type | Interventional |
| Purpose and rationale | This study with Compound of Formula (I), is an adaptive phase 2 study designed to establish safety and efficacy and characterize the dose-response of Compound of Formula (I), in patients with moderate to severe SjS to allow further development of the compound for treatment of this disease. |
| Purpose and rationale | This study with Compound of Formula (I), is an adaptive phase 2 study designed to establish safety and efficacy and characterize the dose-response of Compound of Formula (I), in patients with moderate to severe SjS to allow further development of the compound for treatment of this disease. |
| Primary Objective(s) | The primary objective is to characterize the dose-response relationship of Compound of Formula (I), based on change from baseline in ESSDAI at Week 24. |
| Secondary Objectives | Objective 1: To evaluate the dose-response profile of Compound of Formula (I) based on change from baseline in ESSPRI at Week 24.<br>Objective 2: To evaluate the efficacy of Compound of Formula (I), compared to placebo with respect to change from baseline on patient and physician-reported outcomes (ESSPRI, FACIT-F, EQ-5D, PhGA) over time.<br>Objective 3: To evaluate the efficacy of Compound of Formula (I), or a pharmaceutically acceptable salt thereof, compared to placebo with respect to change from baseline in ESSDAI over time.<br>Objective 4: To evaluate the safety and tolerability of Compound of Formula (I), or a pharmaceutically acceptable salt thereof, by reporting the occurence of treatment emergent AEs (both serious and non-serious), abnormal vital signs, laboratory and ECG values during the study.<br>Objective 5: To assess PK parameters of Compound of Formula (I), or a pharmaceutically acceptable salt thereof, (Cmax, AUC, Tmax and MRT and others as needed) at steady state. |
| Study design | This is an adaptive phase 2 randomized, double-blind, placebo-controlled, multi center, two-part dose-ranging study to evaluate the safety and efficacy of multiple Compound of Formula (I), or a pharmaceutically acceptable salt thereof, doses in patients with moderate to severe Sjögren's Syndrome (SjS) over 24 weeks of treatment. Total study duration for each patient is up to 35 weeks. |
| Population | Female and male patients aged 18 to 75 years with moderate to severe SjS; a total of approximately 252 patients are enrolled. |
| Key Inclusion criteria | Male or female patients aged 18 to 75 years at screening<br>Classification of Sjögren's Syndrome according to the 2016 ACR/EULAR criteria at screening<br>Screening ESSDAI (based on weighted score) ≥5 from 8 defined domains (biologic, hematologic, articular, cutaneous, glandular, lymphadenopathy, renal, constitutional). Patients with involvement of one or more of the remaining 4 domains are eligible but scores of these domains will not contribute to the assessment for eligibility, but are part of the overall ESSDAI score for that subject<br>Screening ESSPRI ≥5<br>Seropositive for anti-Ro/SSA antibodies at or within 3 months prior to screening<br>Unstimulated whole salivary flow rate of >0 mL/min at screening |
| Key Exclusion criteria | Sjögren's Syndrome overlap syndromes where another autoimmune disease constitutes the primary illness<br>Rituximab or other B cell depleting drug within 12 months of Screening. For subjects who received such drug, their B cell count should be within normal range.<br>Prior treatment with any of the following within 6 months of baseline<br>    CTLA4-Fc Ig (abatacept)<br>    Anti-TNF-α mAb<br>    Intravenous Ig<br>    Plasmapheresis<br>    i.v. or oral cyclophosphamide<br>    i.v. or oral cyclosporine A<br>Required regular use of medications known to cause, as a major side effect, dry mouth/eyes, and which have not been on a stable dose for at least 30 days prior to Screening, or any anticipated change in the treatment regimen during the course of the study.<br>Significant bleeding risk or coagulation disorders, including but not limited to:<br>    History or presence of thrombotic or thromboembolic event, or increased risk for thrombotic or thromboembolic event<br>    Requirement for anti-platelet or anticoagulant medication (for example, warfarin, or clopidogrel or Novel Oral Anti-Coagulant-NOAC) other than acetylsalicylic acid (up to 100 mg/d)<br>    History of gastrointestinal or intracerebral or otherwise severe prior bleeding events, including in association with use of Nonsteroidal Anti-Inflammatory Drug (NSAID)<br>Screening CBC laboratory values as follows:<br>    Hemoglobin levels below 10 g/dL<br>    Total leukocyte count less than 3,000/μL<br>    Platelets less than 100,000/μL<br>    Neutrophil count ≤1,500/μL |
| Study treatment | Compound of Formula (I), or a pharmaceutically acceptable salt thereof, capsules<br>Placebo capsules |
| Efficacy assessments | ESSDAI, ESSPRI, FACIT-F, EQ-5D, PhGA |
| Pharmacodynamic assessments | BTK occupancy |
| Pharmacokinetic assessments | PK parameters AUCtau, AUC0-4h, Cmax, Tmax and MRT and others as needed |
| Key safety assessments | Adverse event monitoring<br>Physical examinations<br>Monitoring of laboratory markers in blood and urine<br>Central ECG assessment<br>Additional liver and renal safety monitoring |

| | Protocol summary |
|---|---|
| Data analysis | The dose-response relationship among Compound of Formula (I), or a pharmaceutically acceptable salt thereof, and placebo is characterized with regards to the change from baseline in ESSDAI at Week 24 visit. The generalized MCP-Mod methodology is implemented using ESSDAI measurements from all time points until Week 24 visit to confirm an overall dose-response signal, and to estimate the optimum dose that corresponds to the clinically relevant effect over placebo. Testing is done at one-sided 5% alpha level.<br>The dose-response curves of Compound of Formula (I) based on improvements in ESSPRI at Week 24 visit are estimated using the same MCP-Mod method as for the primary analysis. The change from baseline in ESSDAI, ESSPRI, FACIT-F, EQ-5D and PhGA is analyzed using a MMRM including treatment group, visit, treatment group by visit interaction, stratification factor baseline ESSDAI (<10 or ≥10) and geographic region as fixed factors as well as baseline value of variable analyzed as a covariate. The estimated means per dose and visit and the differences between Compound of Formula (I) treatment groups and placebo are derived together with 2-sided 95% confidence intervals. |

Objectives and Endpoints

TABLE 2-4

Objectives and related endpoints

| Objective(s) | Endpoint(s) |
|---|---|
| Primary objective(s) | Endpoint(s) for primary objective(s) |
| To characterize the dose-response relationship of Compound of Formula (I), or a pharmaceutically acceptable salt thereof, based on change from baseline in ESSDAI at Week 24 | Change from baseline in ESSDAI at Week 24 |
| Secondary objective(s) | Endpoint(s) for secondary objective(s) |
| To evaluate the efficacy of Compound of Formula (I), or a pharmaceutically acceptable salt thereof, compared to placebo with respect to change from baseline on patient- and physician-reported outcomes over time | Change from baseline in ESSPRI, FACIT-F, EQ-5D and PhGA over time |
| To evaluate the dose-response profile of Compound of Formula (I), or a pharmaceutically acceptable salt thereof, based on change in ESSPRI at Week 24. | Change from baseline in ESSPRI at Week 24 |
| To evaluate the efficacy of Compound of Formula (I), or a pharmaceutically acceptable salt thereof, compared to placebo with respect to change from baseline in ESSDAI over time | Change from baseline in ESSDAI over time |
| To evaluate the safety and tolerability of Compound of Formula (I), or a pharmaceutically acceptable salt thereof, | Safety endpoints will include Occurrence of treatment emergent adverse events (both serious and non-serious) during the study<br>Occurrence of treatment emergent abnormal vital signs, laboratory and ECG during the study |

TABLE 2-4-continued

Objectives and related endpoints

| Objective(s) | Endpoint(s) |
|---|---|
| To assess PK parameters of Compound of Formula (I), or a pharmaceutically acceptable salt thereof, | PK parameters AUC, Cmax, Tmax and MRT and others as needed |
| Exploratory objective(s) | Endpoint(s) for exploratory objective(s) |
| To explore the effect of Compound of Formula (I), or a pharmaceutically acceptable salt thereof, on fatigue digitally measured with wearable device over 24 weeks | Changes of physical activity, vital sign parameters and physical fatigue scores measured with wearable device between baseline and 24 weeks of treatment. |
| To explore target engagement of Compound of Formula (I), or a pharmaceutically acceptable salt thereof | BTK occupancy in peripheral blood |
| To explore the effects of Compound of Formula (I), or a pharmaceutically acceptable salt thereof, in self-reported disease burden | Change from baseline in the total score for parameters assessed in patient eDiary (dryness of eye, mouth and skin, physical fatigue, muscle and/or joint pain, genital dryness) |

Study Design

This is an adaptive phase 2 randomized, double-blind, placebo-controlled, multi-center, integrated dose-ranging study to evaluate the safety and efficacy of multiple doses of Compound (I) in patients with moderate to severe Sjögren's Syndrome (SjS). In this study, moderate to severe SjS is defined as Sjögren's Syndrome according to ACR/EULAR criteria and an ESSDAI of at least 5 (in 8 out of 12 domains) and an ESSPRI of at least 5. In case study subjects receive certain concomitant therapy for their underlying disease and still meet entry criteria, they will remain on this therapy provided it remains stable until the end of the study.

The study consists of two parts. In Part 1 of the study, the highest concluded biologically active single dose (100 mg Compound of Formula (I), or a pharmaceutically acceptable salt thereof) is tested in two different dosing regimens: as once daily dose (qd) or twice daily dose (bid) and compared to a Placebo arm. A total of approximately 72 study subjects are equally randomized to these 3 treatment groups for an expected sample size of 24 subjects per group. In Part 2, the dosing regimen selected (qd or bid) is expanded to lower doses to assess the safety and dose-response of this dosing regimen between the concluded lowest (10 mg of Compound of Formula (I)) and highest (100 mg of Compound of Formula (I)) doses. This results in 4 treatment arms; placebo plus Compound of Formula (I) at three dose levels (100 mg bid/qd, 25 mg bid or 35 mg qd and 10 mg bid/qd). A total of approximately 180 subjects are expected to be equally randomized to those 4 treatment arms resulting in a sample size of 45 subjects per group.

Each individual study subject first undergoes a screening period of up to 6 weeks, a treatment duration of 24 weeks and a follow-up period of 30 days post last administration of study treatment, before the End of Study visit. The total duration for each subject in the study, including Screening, is up to 35 weeks.

For the entire duration of the treatment period (24 weeks), subjects receive twice-daily doses of Compound of Formula (I), or placebo, regardless of selected dosing regimen, so that the blind is maintained throughout the entire study.

Safety assessments include physical examinations, ECGs, vital signs, standard clinical laboratory evaluations (hematology, biochemistry and urinalysis) as well as adverse event and serious adverse event monitoring.

Screening

After signing informed consent, subjects are assessed for ESSDAI and ESSPRI as well as completing safety and other assessments to evaluate eligibility. For logistical reasons, assessments are performed on different days, during the 6 week screening period, if deemed appropriate by the Investigator. Subjects that fail screening, can be re-screened for one further occasion. Subjects are also be given guidance on how to use the wearable device (if they have chosen to use it), which they are provided, should they be confirmed as eligible for the study.

Baseline

Eligible subjects return for the Baseline visit on Day 1. Subjects can reside overnight at the site for logistical reasons, although this would not be considered a hospital admission. Eligibility is confirmed prior to randomization and required baseline assessments is to be completed prior to dosing on Day 1. If preferred by the site for scheduling purposes, some Baseline assessments are carried out on the evening prior to Day 1.

Study Treatment

The investigational drug is provided as appropriately blinded labeled bottles. The bottles contain capsules with either 10 mg or 25 mg or 50 mg active substance (Compound of Formula (I)) or matching Placebo. Each dose (2 capsules) is swallowed with water and should be taken on an empty stomach. Between morning and evening doses, a dosing interval of approximately 12 hours (between 10 and 14 hours) should be kept. Details on the requirements for storage and management of study treatment, and instructions to be followed for subject numbering, dispensing and taking study treatment are outlined in the SOM.

Treatment Arms/Group

In Part 1, subjects are assigned on Day 1 to one of the following 3 treatment arms in a ratio of 1:1:1
  Compound of Formula (I), 100 mg bid
  Compound of Formula (I), 100 mg qd
  Placebo
Dosing schedule and dose range for Part 2 are based on data from IAs. In Part 2, subjects are assigned on Day 1 to one of the following 4 treatment arms in a ratio of 1:1:1:1
  Compound of Formula (I), 100 mg bid or qd
  Compound of Formula (I), 35 mg qd or 25 mg bid
  Compound of Formula (I), 10 mg bid or qd
  Placebo
Subjects take 2 capsules at each dose. There is a morning and an evening dose (2 capsules each) for all subjects in both parts.

Subjects receive their morning dose of Compound of Formula (I), or placebo at the site on Days 1 (Week 4), 57 (Week 8), 85 (Week 12), 113 (Week 16), 141 (Week 20) and 169 (Week 24). Other morning doses and all evening doses are taken by the participating subjects generally at home. All subjects receive their respective supply of Compound of Formula (I), or placebo capsules every 4 weeks during their scheduled visits to the site.

Subjects are randomized to the respective treatment arms per study part. Except for Japan, randomization is stratified by baseline ESSDAI (<or ≥10 based on weighted scores). Separate blocks of randomization numbers are generated for subjects in Japan and the other countries participating to ensure that Japanese subjects are equally distributed across all treatment groups in the study. Subjects receive their morning dose of Compound of Formula (I), or placebo at the site on Days 1 (Week 1), 29 (Week 4), 57 (Week 8), 85 (Week 12), 113 (Week 16), 141 (Week 20) and 169 (Week 24). Subjects then are provided study drug and may return home to continue their daily dosing regimen (self-administration). At Week 4 and 24 visits, subjects also undergo post-dose safety and PK assessments.

Subjects return to the site at approximately 4-weekly intervals, with an additional visit at the end of Week 2 (Day 15). At the study visits, subjects undergo ESSDAI and ESSPRI assessments as well as other scales/questionnaires, safety and various PK, PD and biomarker sample collections as indicated in the Assessment Schedule.

Each week, subjects are asked to complete diaries to record their SjS symptoms and administration of treatment.

The primary endpoint of the study is assessed after the completion of 24 week treatment (Day 169; end of Week 24 visit) at the end of Part 2. The interim analyses evaluate efficacy and safety after 12 weeks of treatment as a surrogate of 24-week treatment results in Part 1.

Rationale for Dose/Regimen and Duration of Treatment

Dose/Regimen for Part 1

The highest dose planned for this study (100 mg bid or qd) has demonstrated a maximal effect for Compound of Formula (I) based on predicted BTK occupancy in blood (B-cell blockade) and tissues, and inhibition of CD63 up-regulation in basophils (IB) (results in Example 2). This dose is, therefore, concluded to provide maximum clinical effect in tissue, including lymphatic tissue for SjS. In Phase 1, doses up to 600 mg both as single and multiple doses and 200 mg as twice daily dose had been tested in human volunteers and proven to be safe.

In Part 1, the dose concluded to provide maximal effect (100 mg) is tested in a qd and in a bid regimen and compared to placebo. Due to the covalent nature of the binding of Compound of Formula (I) to intracellular BTK, the duration of the treatment effect is dependent on the turn-over rate of the BTK molecule. Simulation models have shown, that a qd-regimen with 100 mg of compound of Formula (I) at steady state provide an average 83% BTK occupancy 24 hrs after dosing (and immediately prior to the next dose) whereas a bid-regimen with the same single dose of 100 mg has an average 96% BTK-occupancy at 24 hrs.

Furthermore, 70% BTK inhibition for ~90% of each dosing period at steady state is considered to be appropriate for optimal clinical efficacy. Therefore a dosing regimen of 100 mg of Compound (I), both the qd- and bid regimens, which are tested in Part 1 of this study provides efficacy.

Dose/Regimen for Part 2

Part 2 will assess the full dose range of the selected dosing regimen with doses between 10 mg and 100 mg. In the first-in-human study with Compound of Formula (I) administration of 10 mg Compound of Formula (I) q.d. resulted in nearly complete BTK occupancy in blood and a >80% reduction of CD63 up-regulation, however only a minimal inhibition of wheal size in a skin prick test (SPT). It is therefore concluded that 10 mg Compound of Formula (I) q.d. will correspond to the onset of biological activity for pharmacodynamic activity in tissues. As a middle dose, a daily dose of 35 mg Compound of Formula (I) qd or 25 mg bid is considered to be appropriate to accurately describe the full dose-response curve of Compound of Formula (I), qd or bid respectively. Continuation of the double-blind treatment period up to 24 weeks will provide continued safety and efficacy data for Compound of Formula (I).

Rationale for Choice of Control Drug (Placebo)

Comparator treatment is placebo to provide objective evidence of potential AEs and other safety data, as well as clinical efficacy and PD data generated from subjects treated with Compound of Formula (I), or a pharmaceutically acceptable salt thereof, during the 24-week trial. Since there is no approved systemic treatment for SjS, the use of placebo is justified. Current standard-of-care for SjS patients is limited to symptomatic care for the mucosal signs and symptoms (dryness) and steroids and conventional DMARDs are often ineffective. No pharmacologic intervention is effective against the severe, disabling fatigue associated with SjS.

What is claimed is:

1. A method of treating Sjögren's syndrome (SjS) in a subject in need of such treatment, comprising administering to the subject a daily dose of about 10 mg-about 200 mg of a compound of Formula (I):

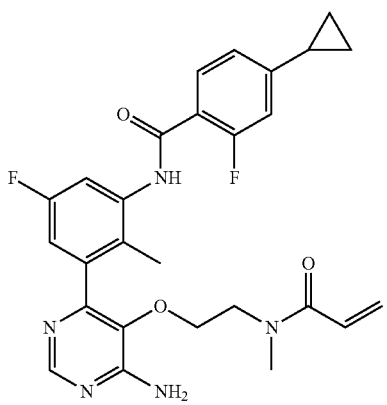

(I)

or a pharmaceutically acceptable salt thereof.

2. The method of claim 1, wherein the daily dose is from about 10 mg to about 100 mg.

3. The method of claim 1, wherein the daily dose is about 100 mg.

4. The method of claim 1, wherein the daily dose is about 50 mg.

5. The method of claim 1, wherein the daily dose is about 35 mg.

6. The method of claim 1, wherein the daily dose is about 25 mg.

7. The method of claim 1, wherein the daily dose is about 20 mg.

8. The method of claim 1, wherein the compound of Formula (I), or a pharmaceutically acceptable salt thereof, is administered once a day in a dose of about 10 mg, about 35 mg, about 50 mg or about 100 mg.

9. The method of claim 1, wherein the compound of Formula (I), or a pharmaceutically acceptable salt thereof, is administered in a dose of about 10 mg, about 25 mg, about 50 mg or about 100 mg twice daily.

10. The method of claim 1, wherein the subject has moderate to severe SjS.

11. The method of claim 1, wherein the subject is selected according to at least one of the following criteria:
   a) prior to treatment with compound of Formula (I), the subject has an ESSPRI score≥5; and
   b) prior to treatment with the compound of Formula (I), the subject has an ESSDAI based on weight score≥5 from 8 defined domains selected from biologic, haemetologic, articular, cutaneous, glandular, lymphadenopathy, renal and constitutional.

12. The method of claim 1, wherein the subject is an adult.

13. The method of claim 11, wherein said subject achieves by week 12 or by week 24 of treatment at least one of the following:
   a) a reduction of the ESSPRI score; and
   b) a reduction of the ESSDAI score.

14. The method of claim 11, wherein said subject achieves a sustained response as measured by ESSPRI or EDSSDAI at week 5 after completion of the treatment.

15. The method of claim 1, wherein the compound of Formula (I), or pharmaceutically acceptable salt thereof, is disposed in a pharmaceutical formulation and wherein the pharmaceutical formulation further comprises a pharmaceutically acceptable carrier.

16. The method of claim 1, wherein the compound of Formula (I), or a pharmaceutically acceptable salt thereof, has a T max of about 0.5-3 hours.

17. The method of claim 1, wherein the daily dose is about 10 mg-about 200 mg of the compound of Formula (I).

18. The method of claim 1, wherein the compound of Formula (I) is administered once a day in a dose of about 10 mg, about 35 mg, about 50 mg or about 100 mg.

19. The method of claim 18, wherein the compound of Formula (I) is administered once a day in a dose of 100 mg.

20. The method of claim 1, wherein the compound of Formula (I) is administered in a dose of about 10 mg, about 25 mg, about 50 mg or about 100 mg twice daily.

21. The method of claim 20, wherein the compound of Formula (I) is administered in a dose of about 100 mg twice daily.

* * * * *